(12) United States Patent
Suttin

(10) Patent No.: US 10,092,379 B2
(45) Date of Patent: Oct. 9, 2018

(54) JIGS FOR PLACING DENTAL IMPLANT ANALOGS IN MODELS AND METHODS OF DOING THE SAME

(71) Applicant: Biomet 3i, LLC, Palm Beach Gardens, FL (US)

(72) Inventor: Zachary B. Suttin, West Palm Beach, FL (US)

(73) Assignee: Biomet 3I, LLC, Palm Beach Gardens, FL (US)

( * ) Notice: Subject to any disclaimer, the term of this patent is extended or adjusted under 35 U.S.C. 154(b) by 320 days.

(21) Appl. No.: 14/560,930

(22) Filed: Dec. 4, 2014

(65) Prior Publication Data

US 2015/0111179 A1 Apr. 23, 2015

Related U.S. Application Data

(62) Division of application No. 13/727,750, filed on Dec. 27, 2012, now Pat. No. 8,926,328.

(51) Int. Cl.
*A61C 13/34* (2006.01)
*A61C 8/00* (2006.01)
(Continued)

(52) U.S. Cl.
CPC .............. *A61C 13/34* (2013.01); *A61C 1/082* (2013.01); *A61C 8/0001* (2013.01);
(Continued)

(58) Field of Classification Search
CPC ....... A61C 13/34; A61C 1/082; A61C 8/0001; A61C 13/0004; A61C 13/08; A61C 13/081; A61C 13/12; A61C 9/0053
See application file for complete search history.

(56) References Cited

U.S. PATENT DOCUMENTS 3,906,634 A 9/1975 Aspel
3,919,772 A 11/1975 Lenczycki
(Continued)

FOREIGN PATENT DOCUMENTS

DE 10029256 A1 11/2000
TW M 442 135 12/2012
(Continued)

OTHER PUBLICATIONS

European Search Report for Application No. EP 13 86 7717.4, dated Sep. 14, 2015 (3 pages).
(Continued)

*Primary Examiner* — Cris L Rodriguez
*Assistant Examiner* — Hao D Mai
(74) *Attorney, Agent, or Firm* — Schwegman Lundberg & Woessner, P.A.

(57) ABSTRACT

A placement jig for locating a dental implant analog in a physical model of a patient's mouth includes a base, a guide-strut receiving feature, a throughbore, and an angled receiving feature. The guide-strut receiving feature is positioned within the base and is configured to receive a guide-strut of the physical model thereby positioning a lower surface of the placement jig at a desired distance from an opening of a bore in the physical model. The throughbore receives a screw therethrough that engages the dental implant analog such that the dental implant analog is removably coupled to the base. The angled receiving feature is positioned about the throughbore on the lower surface of the base. The angled receiving feature includes a mating surface that is configured to abut a custom abutment positioned between the mating surface and the dental implant analog.

20 Claims, 11 Drawing Sheets

(51) Int. Cl.
    *A61C 9/00* (2006.01)
    *A61C 13/00* (2006.01)
    *A61C 13/08* (2006.01)
    *A61C 1/08* (2006.01)
    *A61C 13/12* (2006.01)

(52) U.S. Cl.
    CPC ........ *A61C 9/0053* (2013.01); *A61C 13/0004* (2013.01); *A61C 13/08* (2013.01); *A61C 13/081* (2013.01); *A61C 13/12* (2013.01)

(56) References Cited

U.S. PATENT DOCUMENTS

| | | |
|---|---|---|
| 3,958,471 A | 5/1976 | Muller |
| 4,011,602 A | 3/1977 | Rybicki et al. |
| 4,056,585 A | 11/1977 | Waltke |
| 4,086,701 A | 5/1978 | Kawahara et al. |
| 4,177,562 A | 12/1979 | Miller et al. |
| 4,199,102 A | 4/1980 | Paul |
| 4,294,544 A | 10/1981 | Altschuler et al. |
| 4,306,862 A | 12/1981 | Knox |
| 4,325,373 A | 4/1982 | Slivenko et al. |
| 4,341,312 A | 7/1982 | Scholer |
| 4,364,381 A | 12/1982 | Sher et al. |
| 4,439,152 A | 3/1984 | Small |
| 4,543,953 A | 10/1985 | Slocum et al. |
| 4,547,157 A | 10/1985 | Driskell |
| 4,571,180 A | 2/1986 | Kulick |
| 4,611,288 A | 9/1986 | Duret et al. |
| 4,624,673 A | 11/1986 | Meyer |
| 4,663,720 A | 5/1987 | Duret et al. |
| 4,713,004 A | 12/1987 | Linkow et al. |
| 4,756,689 A | 7/1988 | Lundgren |
| 4,758,161 A | 7/1988 | Niznick |
| 4,767,331 A | 8/1988 | Hoe |
| 4,772,204 A | 9/1988 | Soderberg |
| 4,821,200 A | 4/1989 | Öberg |
| 4,842,518 A | 6/1989 | Linkow et al. |
| 4,850,870 A | 7/1989 | Lazzara et al. |
| 4,850,873 A | 7/1989 | Lazzara et al. |
| 4,854,872 A | 8/1989 | Detsch |
| 4,856,994 A | 8/1989 | Lazzara et al. |
| 4,872,839 A | 10/1989 | Brajnovic |
| 4,906,191 A | 3/1990 | Soderberg |
| 4,906,420 A | 3/1990 | Brajnovic |
| 4,931,016 A | 6/1990 | Sillard |
| 4,935,635 A | 6/1990 | O'Harra |
| 4,961,674 A | 10/1990 | Wang et al. |
| 4,964,770 A | 10/1990 | Steinbichler et al. |
| 4,986,753 A | 1/1991 | Sellers |
| 4,988,297 A | 1/1991 | Lazzara et al. |
| 4,988,298 A | 1/1991 | Lazzara et al. |
| 4,998,881 A | 3/1991 | Lauks |
| 5,000,685 A | 3/1991 | Brajnovic |
| 5,006,069 A | 4/1991 | Lazzara et al. |
| 5,015,183 A | 5/1991 | Fenick |
| 5,015,186 A | 5/1991 | Detsch |
| 5,030,096 A | 7/1991 | Hurson et al. |
| 5,035,619 A | 7/1991 | Daftary |
| 5,040,982 A | 8/1991 | Stefan-Dogar |
| 5,040,983 A | 8/1991 | Binon |
| 5,064,375 A | 11/1991 | Jörnéus |
| 5,071,351 A | 12/1991 | Green, Jr. et al. |
| 5,073,111 A | 12/1991 | Daftary |
| 5,087,200 A | 2/1992 | Brajnovic et al. |
| 5,100,323 A | 3/1992 | Friedman et al. |
| 5,104,318 A | 4/1992 | Piche et al. |
| 5,106,300 A | 4/1992 | Voitik |
| 5,122,059 A | 6/1992 | Dürr et al. |
| 5,125,839 A | 6/1992 | Ingber et al. |
| 5,125,841 A | 6/1992 | Carlsson et al. |
| 5,133,660 A | 7/1992 | Fenick |
| 5,135,395 A | 8/1992 | Marlin |
| 5,145,371 A | 9/1992 | Jörnéus |
| 5,145,372 A | 9/1992 | Daftary et al. |
| 5,176,516 A | 1/1993 | Koizumi |
| 5,188,800 A | 2/1993 | Green, Jr. et al. |
| 5,195,892 A | 3/1993 | Gersberg |
| 5,205,745 A | 4/1993 | Kamiya et al. |
| 5,209,659 A | 5/1993 | Friedman et al. |
| 5,209,666 A | 5/1993 | Balfour et al. |
| 5,213,502 A | 5/1993 | Daftary |
| 5,221,204 A | 6/1993 | Kruger et al. |
| 5,237,998 A | 8/1993 | Duret et al. |
| 5,246,370 A | 9/1993 | Coatoam |
| 5,257,184 A | 10/1993 | Mushabac |
| 5,281,140 A | 1/1994 | Niznick |
| 5,286,195 A | 2/1994 | Clostermann |
| 5,286,196 A | 2/1994 | Brajnovic et al. |
| 5,292,252 A | 3/1994 | Nickerson et al. |
| 5,297,963 A | 3/1994 | Dafatry |
| 5,302,125 A | 4/1994 | Kownacki et al. |
| 5,312,254 A | 5/1994 | Rosenlicht |
| 5,312,409 A | 5/1994 | McLaughlin et al. |
| 5,316,476 A | 5/1994 | Krauser |
| 5,320,529 A | 6/1994 | Pompa |
| 5,328,371 A | 7/1994 | Hund et al. |
| 5,334,024 A | 8/1994 | Niznick |
| 5,336,090 A | 8/1994 | Wilson, Jr. et al. |
| 5,338,196 A | 8/1994 | Beaty et al. |
| 5,338,198 A | 8/1994 | Wu et al. |
| 5,343,391 A | 8/1994 | Mushabac |
| 5,344,457 A | 9/1994 | Pilliar et al. |
| 5,350,297 A | 9/1994 | Cohen |
| 5,359,511 A | 10/1994 | Schroeder et al. |
| 5,362,234 A | 11/1994 | Salazar et al. |
| 5,362,235 A | 11/1994 | Daftary |
| 5,368,483 A | 11/1994 | Sutter et al. |
| 5,370,692 A | 12/1994 | Fink |
| 5,372,502 A | 12/1994 | Massen et al. |
| 5,386,292 A | 1/1995 | Massen et al. |
| 5,413,481 A | 5/1995 | Göppel et al. |
| 5,417,569 A | 5/1995 | Perisse |
| 5,417,570 A | 5/1995 | Zuest et al. |
| 5,419,702 A | 5/1995 | Beaty et al. |
| 5,431,567 A | 7/1995 | Datary |
| 5,437,551 A | 8/1995 | Chalifoux |
| 5,440,393 A | 8/1995 | Wenz |
| 5,452,219 A | 9/1995 | Dehoff et al. |
| 5,458,488 A | 10/1995 | Chalifoux |
| 5,476,382 A | 12/1995 | Daftary |
| 5,476,383 A | 12/1995 | Beaty et al. |
| 5,492,471 A | 2/1996 | Singer |
| 5,516,288 A | 5/1996 | Sichler et al. |
| 5,527,182 A | 6/1996 | Willoughby |
| 5,533,898 A | 7/1996 | Mena |
| 5,538,426 A | 7/1996 | Harding et al. |
| 5,547,377 A | 8/1996 | Daftary |
| 5,556,278 A | 9/1996 | Meitner |
| 5,564,921 A | 10/1996 | Marlin |
| 5,564,924 A | 10/1996 | Kwan |
| 5,569,578 A | 10/1996 | Mushabac |
| 5,575,656 A | 11/1996 | Hajjar |
| 5,580,244 A | 12/1996 | White |
| 5,580,246 A | 12/1996 | Fried |
| 5,595,703 A | 1/1997 | Swaelens et al. |
| 5,613,832 A | 3/1997 | Su |
| 5,613,852 A | 3/1997 | Bavitz |
| 5,617,994 A | 4/1997 | Friedrich |
| 5,630,717 A | 5/1997 | Zuest |
| 5,636,986 A | 6/1997 | Prezeshkian |
| 5,651,675 A | 7/1997 | Singer |
| 5,652,709 A | 7/1997 | Andersson et al. |
| 5,658,147 A | 8/1997 | Phimmasone |
| 5,662,476 A | 9/1997 | Ingber et al. |
| 5,674,069 A | 10/1997 | Osorio |
| 5,674,071 A | 10/1997 | Beaty et al. |
| 5,674,073 A | 10/1997 | Ingber et al. |
| 5,681,167 A | 10/1997 | Lazarof |
| 5,685,715 A | 11/1997 | Beaty et al. |
| 5,688,283 A | 11/1997 | Knapp |
| 5,692,904 A | 12/1997 | Beaty et al. |
| 5,704,936 A | 1/1998 | Mazel |
| 5,718,579 A | 2/1998 | Kennedy |

(56) References Cited

U.S. PATENT DOCUMENTS

| | | |
|---|---|---|
| 5,725,376 A | 3/1998 | Poirier |
| 5,733,124 A | 3/1998 | Kwan |
| 5,741,215 A | 4/1998 | D'Urso |
| 5,743,916 A | 4/1998 | Greenberg |
| 5,759,036 A | 6/1998 | Hinds |
| 5,762,125 A | 6/1998 | Mastrorio |
| 5,762,500 A | 6/1998 | Lazarof |
| 5,768,134 A | 6/1998 | Swaelens et al. |
| 5,769,636 A | 6/1998 | Di Sario |
| 5,791,902 A | 8/1998 | Lauks |
| 5,800,168 A | 9/1998 | Cascione et al. |
| 5,813,858 A | 9/1998 | Singer |
| 5,823,778 A | 10/1998 | Schmitt et al. |
| 5,842,859 A | 12/1998 | Palacci |
| 5,846,079 A | 12/1998 | Knode |
| 5,851,115 A | 12/1998 | Carlsson et al. |
| 5,857,853 A | 1/1999 | Van Nifterick et al. |
| 5,871,358 A | 2/1999 | Ingber et al. |
| 5,873,722 A | 2/1999 | Lazzara et al. |
| 5,876,204 A | 3/1999 | Day et al. |
| 5,885,078 A | 3/1999 | Cagna et al. |
| 5,888,034 A | 3/1999 | Greenberg |
| 5,904,483 A | 5/1999 | Wade |
| 5,915,962 A | 6/1999 | Rosenlicht |
| 5,927,982 A | 7/1999 | Kruger |
| 5,938,443 A | 8/1999 | Lazzara et al. |
| 5,954,769 A | 9/1999 | Rosenlicht |
| 5,964,591 A | 10/1999 | Beaty et al. |
| 5,967,777 A | 10/1999 | Klein et al. |
| 5,984,681 A | 11/1999 | Huang |
| 5,989,025 A | 11/1999 | Conley |
| 5,989,029 A | 11/1999 | Osorio |
| 5,989,258 A | 11/1999 | Hattori |
| 5,992,229 A | 11/1999 | Pyotsia et al. |
| 5,997,681 A | 12/1999 | Kinzie |
| 6,000,939 A | 12/1999 | Ray et al. |
| 6,008,905 A | 12/1999 | Breton et al. |
| 6,068,479 A | 5/2000 | Kwan |
| 6,099,311 A | 8/2000 | Wagner et al. |
| 6,099,313 A | 8/2000 | Dorken et al. |
| 6,099,314 A | 8/2000 | Kopelman et al. |
| 6,120,293 A | 9/2000 | Lazzara et al. |
| 6,129,548 A | 10/2000 | Lazzara et al. |
| 6,135,773 A | 10/2000 | Lazzara |
| 6,142,782 A | 11/2000 | Lazarof |
| 6,174,168 B1 | 1/2001 | Dehoff et al. |
| 6,175,413 B1 | 1/2001 | Lucas |
| 6,190,169 B1 | 2/2001 | Bluemli et al. |
| 6,296,483 B1 | 2/2001 | Champleboux |
| 6,197,410 B1 | 3/2001 | Vallittu et al. |
| 6,200,125 B1 | 3/2001 | Akutagawa |
| 6,206,693 B1 | 3/2001 | Hultgren |
| 6,209,794 B1 | 4/2001 | Webster et al. |
| 6,210,162 B1 | 4/2001 | Chishti |
| 6,217,334 B1 | 4/2001 | Hultgren |
| 6,227,859 B1 | 5/2001 | Sutter |
| 6,283,753 B1 | 9/2001 | Willoughby |
| 6,287,119 B1 | 9/2001 | van Nifterick |
| 6,305,939 B1 | 10/2001 | Dawood |
| 6,319,000 B1 | 11/2001 | Branemark |
| 6,322,728 B1 | 11/2001 | Brodkin |
| 6,382,975 B1 | 5/2002 | Poirier |
| 6,402,707 B1 | 6/2002 | Ernst |
| 6,431,867 B1 | 8/2002 | Gittelson et al. |
| 6,488,503 B1 | 12/2002 | Lichkus et al. |
| 6,497,574 B1 | 12/2002 | Miller |
| 6,540,784 B2 | 4/2003 | Barlow |
| 6,558,162 B1 | 5/2003 | Porter et al. |
| 6,568,936 B2 | 5/2003 | MacDougald |
| 6,575,751 B1 | 6/2003 | Lehmann et al. |
| 6,594,539 B1 | 7/2003 | Geng |
| 6,610,079 B1 | 8/2003 | Li |
| 6,619,958 B2 | 9/2003 | Beaty et al. |
| 6,629,840 B2 | 10/2003 | Chishti |
| 6,634,883 B2 | 10/2003 | Ranalli |
| 6,648,640 B2 | 11/2003 | Rubbert et al. |
| 6,671,539 B2 | 12/2003 | Gateno et al. |
| 6,672,870 B2 | 1/2004 | Knapp |
| 6,688,887 B2 | 2/2004 | Morgan |
| 6,691,764 B2 | 2/2004 | Embert |
| 6,743,491 B2 | 6/2004 | Cirincione et al. |
| 6,755,652 B2 | 6/2004 | Nanni |
| 6,772,026 B2 | 8/2004 | Bradbury |
| 6,776,614 B2 | 8/2004 | Wiechmann et al. |
| 6,783,359 B2 | 8/2004 | Kapit |
| 6,790,040 B2 | 9/2004 | Amber et al. |
| 6,793,491 B2 | 9/2004 | Klein et al. |
| 6,808,659 B2 | 10/2004 | Schulman |
| 6,814,575 B2 | 11/2004 | Poirier |
| 6,821,462 B2 | 11/2004 | Schulamn et al. |
| 6,829,498 B2 | 12/2004 | Kipke et al. |
| D503,804 S | 4/2005 | Phleps et al. |
| 6,882,894 B2 | 4/2005 | Durbin et al. |
| 6,885,464 B1 | 4/2005 | Pfeiffer et al. |
| 6,902,401 B2 | 6/2005 | Jorneus et al. |
| 6,913,463 B2 | 7/2005 | Blacklock |
| 6,926,442 B2 | 8/2005 | Stöckl |
| 6,926,525 B1 | 8/2005 | Ronvig |
| 6,939,489 B2 | 9/2005 | Moszner et al. |
| 6,942,699 B2 | 9/2005 | Stone et al. |
| 6,953,383 B2 | 10/2005 | Rothenberger |
| 6,957,118 B2 | 10/2005 | Kopelman et al. |
| 6,966,772 B2 | 11/2005 | Malin et al. |
| 6,970,760 B2 | 11/2005 | Wolf et al. |
| 6,971,877 B2 | 12/2005 | Harter |
| 6,994,549 B2 | 2/2006 | Brodkin et al. |
| 7,010,150 B1 | 3/2006 | Pfeiffer et al. |
| 7,010,153 B2 | 3/2006 | Zimmermann |
| 7,012,988 B2 | 3/2006 | Adler et al. |
| 7,018,207 B2 | 3/2006 | Prestipino |
| 7,021,934 B2 | 4/2006 | Aravena |
| 7,029,275 B2 | 4/2006 | Rubbert et al. |
| 7,044,735 B2 | 5/2006 | Malin |
| 7,056,115 B2 | 6/2006 | Phan et al. |
| 7,056,472 B1 | 6/2006 | Behringer |
| 7,059,856 B2 | 6/2006 | Marotta |
| 7,066,736 B2 | 6/2006 | Kumar et al. |
| 7,084,868 B2 | 8/2006 | Farag et al. |
| 7,086,860 B2 | 8/2006 | Schuman et al. |
| 7,097,451 B2 | 8/2006 | Tang |
| 7,104,795 B2 | 9/2006 | Dadi |
| 7,110,844 B2 | 9/2006 | Kopelman |
| 7,112,065 B2 | 9/2006 | Kopelman |
| 7,118,375 B2 | 10/2006 | Durbin et al. |
| D532,991 S | 12/2006 | Gozzi |
| 7,153,132 B2 | 12/2006 | Tedesco |
| 7,153,135 B1 | 12/2006 | Thomas |
| 7,163,443 B2 | 1/2007 | Basler et al. |
| 7,175,434 B2 | 2/2007 | Brajnovic |
| 7,175,435 B2 | 2/2007 | Andersson et al. |
| 7,178,731 B2 | 2/2007 | Basler |
| 7,214,062 B2 | 5/2007 | Morgan |
| 7,220,124 B2 | 5/2007 | Taub et al. |
| 7,228,191 B2 | 6/2007 | Hofmeister et al. |
| 7,236,842 B2 | 6/2007 | Kopelman et al. |
| 7,281,927 B2 | 10/2007 | Marotta |
| 7,286,954 B2 | 10/2007 | Kopelman et al. |
| 7,303,420 B2 | 12/2007 | Huch et al. |
| 7,319,529 B2 | 1/2008 | Babayoff |
| 7,322,746 B2 | 1/2008 | Beckhaus et al. |
| 7,322,824 B2 | 1/2008 | Schmitt |
| 7,324,680 B2 | 1/2008 | Zimmermann |
| 7,329,122 B1 | 2/2008 | Scott |
| 7,333,874 B2 | 2/2008 | Taub et al. |
| 7,335,876 B2 | 2/2008 | Eiff et al. |
| D565,184 S | 3/2008 | Royzen |
| 7,367,801 B2 | 5/2008 | Saliger |
| 7,379,584 B2 | 5/2008 | Rubbert et al. |
| D571,471 S | 6/2008 | Stöckl |
| 7,381,191 B2 | 6/2008 | Fallah |
| 7,383,094 B2 | 6/2008 | Kopelman et al. |
| D575,747 S | 8/2008 | Abramovich et al. |
| 7,421,608 B2 | 9/2008 | Schron |
| 7,425,131 B2 | 9/2008 | Amber et al. |

(56) References Cited

U.S. PATENT DOCUMENTS

| | | |
|---|---|---|
| 7,429,175 B2 | 9/2008 | Gittelson |
| 7,435,088 B2 | 10/2008 | Brajnovic |
| 7,442,040 B2 | 10/2008 | Kuo |
| 7,476,100 B2 | 1/2009 | Kuo |
| 7,481,647 B2 | 1/2009 | Sambu et al. |
| 7,488,174 B2 | 2/2009 | Kopelman et al. |
| 7,497,619 B2 | 3/2009 | Stoeckl |
| 7,497,983 B2 | 3/2009 | Khan et al. |
| 7,520,747 B2 | 4/2009 | Stonisch |
| 7,522,764 B2 | 4/2009 | Schwotzer |
| 7,534,266 B2 | 5/2009 | Kluger |
| 7,536,234 B2 | 5/2009 | Kopelman et al. |
| 7,545,372 B2 | 6/2009 | Kopelman et al. |
| 7,551,760 B2 | 6/2009 | Scharlack et al. |
| 7,555,403 B2 | 6/2009 | Kopelman et al. |
| 7,556,496 B2 | 7/2009 | Cinader, Jr. et al. |
| 7,559,692 B2 | 7/2009 | Beckhaus et al. |
| 7,563,397 B2 | 7/2009 | Schulman et al. |
| D597,769 S | 8/2009 | Richter et al. |
| 7,572,058 B2 | 8/2009 | Pruss et al. |
| 7,572,125 B2 | 8/2009 | Brajnovic |
| 7,574,025 B2 | 8/2009 | Feldman |
| 7,578,673 B2 | 8/2009 | Wen et al. |
| 7,580,502 B2 | 8/2009 | Dalpiaz et al. |
| 7,581,951 B2 | 9/2009 | Lehmann et al. |
| 7,582,855 B2 | 9/2009 | Pfeiffer |
| 7,600,999 B2 | 10/2009 | Knopp |
| 7,610,910 B2 | 11/2009 | Ahmed |
| 7,628,537 B2 | 12/2009 | Schulze-Ganzlin |
| 7,632,097 B2 | 12/2009 | Clerck |
| 7,653,455 B2 | 1/2010 | Cnader, Jr. et al. |
| 7,654,823 B2 | 2/2010 | Dadi |
| 7,655,586 B1 | 2/2010 | Brodkin et al. |
| 7,658,610 B2 | 2/2010 | Knopp |
| 7,661,956 B2 | 2/2010 | Powell et al. |
| 7,661,957 B2 | 2/2010 | Tanimura |
| 7,665,989 B2 | 2/2010 | Brajnovic et al. |
| 7,679,723 B2 | 3/2010 | Schwotzer |
| 7,687,754 B2 | 3/2010 | Eiff et al. |
| 7,689,308 B2 | 3/2010 | Holzner et al. |
| D614,210 S | 4/2010 | Basler et al. |
| 7,698,014 B2 | 4/2010 | Dunne et al. |
| 7,774,084 B2 | 8/2010 | Cinader, Jr. |
| 7,780,907 B2 | 8/2010 | Schmidt et al. |
| 7,785,007 B2 | 8/2010 | Stoeckl |
| 7,787,132 B2 | 8/2010 | Körner et al. |
| 7,796,811 B2 | 9/2010 | Orth et al. |
| 7,798,708 B2 | 9/2010 | Erhardt et al. |
| 7,801,632 B2 | 9/2010 | Orth et al. |
| 7,815,371 B2 | 10/2010 | Schulze-Ganzlin |
| 7,824,181 B2 | 11/2010 | Sers |
| D629,908 S | 12/2010 | Jerger et al. |
| 7,855,354 B2 | 12/2010 | Eiff |
| 7,865,261 B2 | 1/2011 | Pfeiffer |
| 7,876,877 B2 | 1/2011 | Stockl |
| 7,901,209 B2 | 3/2011 | Saliger et al. |
| 7,982,731 B2 | 7/2011 | Orth et al. |
| 7,985,119 B2 | 7/2011 | Basler et al. |
| 7,986,415 B2 | 7/2011 | Thiel et al. |
| 7,988,449 B2 | 8/2011 | Amber et al. |
| 8,011,925 B2 | 9/2011 | Powell et al. |
| 8,011,927 B2 | 9/2011 | Merckmans, III et al. |
| 8,026,943 B2 | 9/2011 | Weber et al. |
| 8,038,440 B2 | 10/2011 | Swaelens et al. |
| 8,047,895 B2 | 11/2011 | Basler |
| 8,057,912 B2 | 11/2011 | Basler et al. |
| 8,062,034 B2 | 11/2011 | Hanisch et al. |
| 8,083,522 B2 | 12/2011 | Karkar et al. |
| 8,105,081 B2 | 1/2012 | Bavar |
| 2001/0008751 A1 | 7/2001 | Chishti et al. |
| 2001/0034010 A1 | 10/2001 | MacDougald et al. |
| 2002/0010568 A1 | 1/2002 | Rubbert et al. |
| 2002/0016639 A1 | 2/2002 | Smith et al. |
| 2002/0028418 A1 | 3/2002 | Farag et al. |
| 2002/0039717 A1 | 4/2002 | Amber et al. |
| 2002/0052606 A1 | 5/2002 | Bonutti |
| 2002/0160337 A1 | 10/2002 | Klein et al. |
| 2002/0167100 A1 | 11/2002 | Moszner |
| 2003/0130605 A1 | 7/2003 | Besek |
| 2003/0222366 A1 | 12/2003 | Stangel |
| 2004/0029074 A1 | 2/2004 | Brajnovic |
| 2004/0048227 A1 | 3/2004 | Brajnovic |
| 2004/0157188 A1 | 8/2004 | Luth et al. |
| 2004/0180308 A1 | 9/2004 | Ebi et al. |
| 2004/0193326 A1 | 9/2004 | Phillips et al. |
| 2004/0219477 A1 | 11/2004 | Harter |
| 2004/0219479 A1 | 11/2004 | Malin et al. |
| 2004/0219490 A1 | 11/2004 | Gartner et al. |
| 2004/0220691 A1 | 11/2004 | Hofmeister et al. |
| 2004/0229185 A1 | 11/2004 | Knopp |
| 2004/0241611 A1 | 12/2004 | Amber et al. |
| 2004/0243481 A1 | 12/2004 | Bradbury et al. |
| 2004/0253562 A1 | 12/2004 | Knopp |
| 2004/0259051 A1 | 12/2004 | Brajnovic |
| 2005/0023710 A1 | 2/2005 | Brodkin et al. |
| 2005/0042569 A1 | 2/2005 | Phan et al. |
| 2005/0056350 A1 | 3/2005 | Dolabdjian et al. |
| 2005/0064360 A1 | 3/2005 | Wen et al. |
| 2005/0070782 A1 | 3/2005 | Brodkin |
| 2005/0084144 A1 | 4/2005 | Feldman |
| 2005/0100861 A1 | 5/2005 | Choi et al. |
| 2005/0136374 A1 | 6/2005 | Carmichael et al. |
| 2005/0170311 A1 | 8/2005 | Tardieu et al. |
| 2005/0177266 A1 | 8/2005 | Kopelman et al. |
| 2005/0271996 A1 | 12/2005 | Sporbert et al. |
| 2005/0277089 A1 | 12/2005 | Brajnovic |
| 2005/0277090 A1 | 12/2005 | Anderson et al. |
| 2005/0277091 A1 | 12/2005 | Andersson et al. |
| 2005/0282106 A1 | 12/2005 | Sussman et al. |
| 2005/0283065 A1 | 12/2005 | Babayoff |
| 2006/0006561 A1 | 1/2006 | Brajnovic |
| 2006/0008763 A1 | 1/2006 | Brajnovic |
| 2006/0008770 A1 | 1/2006 | Brajnovic et al. |
| 2006/0084030 A1 | 4/2006 | Phan et al. |
| 2006/0093988 A1 | 5/2006 | Swaelens et al. |
| 2006/0094951 A1 | 5/2006 | Dean et al. |
| 2006/0127848 A1 | 6/2006 | Sogo et al. |
| 2006/0127855 A1* | 6/2006 | Wen ............... A61C 7/002 433/213 |
| 2006/0127856 A1 | 6/2006 | Wen |
| 2006/0154207 A1 | 7/2006 | Kuo |
| 2006/0199145 A1* | 9/2006 | Liu ............... A61C 9/002 433/49 |
| 2006/0210949 A1 | 9/2006 | Stoop |
| 2006/0257817 A1 | 11/2006 | Shelton |
| 2006/0263741 A1 | 11/2006 | Imgrund et al. |
| 2006/0278663 A1 | 12/2006 | Mink et al. |
| 2006/0281041 A1 | 12/2006 | Rubbert et al. |
| 2007/0009855 A1 | 1/2007 | Stonisch |
| 2007/0015111 A1 | 1/2007 | Kopelman et al. |
| 2007/0031790 A1 | 2/2007 | Raby et al. |
| 2007/0065777 A1 | 3/2007 | Becker |
| 2007/0077532 A1 | 4/2007 | Harter |
| 2007/0092854 A1 | 4/2007 | Powell et al. |
| 2007/0141525 A1 | 6/2007 | Cinader, Jr. |
| 2007/0211081 A1 | 9/2007 | Quadling et al. |
| 2007/0218426 A1 | 9/2007 | Quadling et al. |
| 2007/0264612 A1 | 11/2007 | Mount |
| 2007/0269769 A1 | 11/2007 | Marchesi |
| 2007/0281277 A1 | 12/2007 | Brajnovic |
| 2008/0015740 A1 | 1/2008 | Osann, Jr. |
| 2008/0038692 A1 | 2/2008 | Andersson et al. |
| 2008/0044794 A1 | 2/2008 | Brajnovic |
| 2008/0057467 A1 | 3/2008 | Gittelson |
| 2008/0064005 A1 | 3/2008 | Meitner |
| 2008/0070181 A1 | 3/2008 | Abolfathi et al. |
| 2008/0085489 A1 | 4/2008 | Schmitt |
| 2008/0090210 A1 | 4/2008 | Brajnovic |
| 2008/0096152 A1 | 4/2008 | Cheang |
| 2008/0114371 A1 | 5/2008 | Kluger |
| 2008/0118895 A1 | 5/2008 | Brajnovic |
| 2008/0124676 A1 | 5/2008 | Marotta |
| 2008/0153060 A1 | 6/2008 | De Moyer |
| 2008/0153061 A1 | 6/2008 | Marcello |

(56) References Cited

U.S. PATENT DOCUMENTS

| | | |
|---|---|---|
| 2008/0153065 A1 | 6/2008 | Brajnovic et al. |
| 2008/0153069 A1 | 6/2008 | Holzner et al. |
| 2008/0160485 A1 | 7/2008 | Touchstone |
| 2008/0161976 A1 | 7/2008 | Stanimirovic |
| 2008/0166681 A1 | 7/2008 | Weinstein et al. |
| 2008/0176187 A1* | 7/2008 | Stumpel ............... A61C 1/084 433/196 |
| 2008/0176189 A1 | 7/2008 | Stonisch |
| 2008/0206714 A1 | 8/2008 | Schmitt |
| 2008/0233537 A1 | 9/2008 | Amber et al. |
| 2008/0241798 A1 | 10/2008 | Holzner et al. |
| 2008/0261165 A1 | 10/2008 | Steingart et al. |
| 2008/0281472 A1 | 11/2008 | Podgemy et al. |
| 2008/0286722 A1 | 11/2008 | Berckmans, III et al. |
| 2008/0300716 A1 | 12/2008 | Kopelman et al. |
| 2009/0017418 A1 | 1/2009 | Gittelson |
| 2009/0026643 A1 | 1/2009 | Wiest et al. |
| 2009/0042167 A1 | 2/2009 | Van Der Zel |
| 2009/0081616 A1 | 3/2009 | Pfeiffer |
| 2009/0087817 A1 | 4/2009 | Jansen et al. |
| 2009/0092948 A1 | 4/2009 | Gantes |
| 2009/0098510 A1 | 4/2009 | Zhang |
| 2009/0098511 A1 | 4/2009 | Zhang |
| 2009/0123045 A1 | 5/2009 | Quadling et al. |
| 2009/0123887 A1 | 5/2009 | Brajnovic |
| 2009/0130630 A1 | 5/2009 | Suttin et al. |
| 2009/0187393 A1 | 7/2009 | Van Lierde et al. |
| 2009/0220134 A1 | 9/2009 | Cahill et al. |
| 2009/0220916 A1 | 9/2009 | Fisker et al. |
| 2009/0220917 A1 | 9/2009 | Jensen |
| 2009/0239197 A1 | 9/2009 | Brajnovic |
| 2009/0239200 A1 | 9/2009 | Brajnovic et al. |
| 2009/0253097 A1 | 10/2009 | Brajnovic |
| 2009/0259343 A1 | 10/2009 | Rasmussen et al. |
| 2009/0263764 A1 | 10/2009 | Berckmans, III et al. |
| 2009/0281667 A1 | 11/2009 | Masui et al. |
| 2009/0287332 A1 | 11/2009 | Adusumilli et al. |
| 2009/0298009 A1 | 12/2009 | Brajnovic |
| 2009/0298017 A1 | 12/2009 | Boerjes et al. |
| 2009/0317763 A1 | 12/2009 | Brajnovic |
| 2009/0325122 A1 | 12/2009 | Brajnovic et al. |
| 2010/0009314 A1 | 1/2010 | Tardieu et al. |
| 2010/0021859 A1 | 1/2010 | Kopelman |
| 2010/0028827 A1 | 2/2010 | Andersson et al. |
| 2010/0035201 A1 | 2/2010 | Beck |
| 2010/0038807 A1 | 2/2010 | Brodkin et al. |
| 2010/0075275 A1 | 3/2010 | Brajnovic |
| 2010/0092904 A1 | 4/2010 | Esposti et al. |
| 2010/0105008 A1 | 4/2010 | Powell et al. |
| 2010/0159412 A1 | 6/2010 | Moss et al. |
| 2010/0159413 A1 | 6/2010 | Kuo |
| 2010/0173260 A1 | 7/2010 | Sogo et al. |
| 2010/0280798 A1 | 11/2010 | Pattijn et al. |
| 2011/0008751 A1 | 1/2011 | Pettersson |
| 2011/0010014 A1 | 1/2011 | Oexman et al. |
| 2011/0060558 A1 | 3/2011 | Pettersson |
| 2011/0129792 A1 | 6/2011 | Berckmans, III et al. |
| 2011/0151399 A1 | 6/2011 | DeClerck et al. |
| 2011/0183289 A1 | 7/2011 | Powell et al. |
| 2011/0191081 A1 | 8/2011 | Malfliet et al. |
| 2011/0200970 A1 | 8/2011 | Berckmans, III et al. |
| 2011/0244426 A1 | 10/2011 | Amber et al. |
| 2011/0269104 A1 | 11/2011 | Berckmans, III et al. |
| 2011/0275032 A1 | 11/2011 | Tardieu et al. |
| 2011/0306008 A1 | 12/2011 | Suttin et al. |
| 2011/0306009 A1 | 12/2011 | Suttin et al. |
| 2012/0010740 A1 | 1/2012 | Swaelens et al. |
| 2012/0164593 A1 | 6/2012 | Bavar |
| 2012/0164893 A1 | 6/2012 | Misuzuka et al. |
| 2014/0057227 A1 | 2/2014 | Cheng et al. |

FOREIGN PATENT DOCUMENTS

| | | |
|---|---|---|
| WO | WO 1994/026200 | 11/1994 |
| WO | WO 99/32045 A1 | 7/1999 |
| WO | WO 00/08415 A1 | 2/2000 |
| WO | WO 01/58379 A1 | 8/2001 |
| WO | WO 02/053055 A1 | 7/2002 |
| WO | WO 03/024352 A1 | 3/2003 |
| WO | WO 2004/030565 A1 | 4/2004 |
| WO | WO 2004/075771 A1 | 9/2004 |
| WO | WO 2004/087000 A1 | 10/2004 |
| WO | WO 2004/098435 A2 | 11/2004 |
| WO | WO 2006/014130 A1 | 2/2006 |
| WO | WO 2006/062459 A1 | 6/2006 |
| WO | WO 2006/082198 A1 | 8/2006 |
| WO | WO 2007/005490 A2 | 1/2007 |
| WO | WO 2007/033157 A2 | 3/2007 |
| WO | WO 2007/104842 A1 | 9/2007 |
| WO | WO 2007/129955 A1 | 11/2007 |
| WO | WO 2008/057955 A2 | 5/2008 |
| WO | WO2008/083857 A1 | 7/2008 |
| WO | WO2009/146164 A1 | 12/2009 |
| WO | WO 2012/095851 | 7/2012 |

OTHER PUBLICATIONS

Biomet 3i—Manual entitled "Navigator™ System for CT Guided Surgery Manual", Revision A Oct. 2007—34 pages.

Francois Goulette, "A New Method and a Clinical case for Computer Assisted Dental Implantology." Retrieved from Summer European university in surgical Robotics, URL:www.lirmm.fr/manifs/UEE/docs/students/goulette.pdf, Sep. 6, 2003 (7 pages).

Jakob Brief, "Accuracy of image-guided implantology." Retrieved from Google, <URL:sitemaker.umich.edu/sarmentlab/files/robodent_vs_denx_coir_05.pdf, Aug. 20, 2004 (7 pages).

Machine Design: "Robots are ready for medical manufacturing." Retrieved from MachineDesign.Com, <URL: http://machinedesign.com/article/robots-are-ready-for-medical-manufacturing-0712>, Jul. 12, 2007 (7 pages).

MedNEWS: "'Surgical Glue' May Help to Eliminate Suturing for Implants." Retrieved from MediNEWS.Direct, URL:http://www.medinewsdirect.com/?p=377, Dec. 21, 2007 (1 page).

International Search Report dated Apr. 21, 2014, which issued in corresponding International Patent Application No. PCT-US13-73864 (5 pages).

International Written Opinion dated Apr. 21, 2014 which issued in corresponding International Patent Application No. PCT-US13-73864 (9 pages).

"European Application Serial No. 13867717.4, Examination Notification Art. 94(3) dated Oct. 12, 2015", 5 pgs.

"European Application Serial No. 13867717.4, Response filed Apr. 22, 2016 to Examination Notification Art. 94(3) dated Oct. 12, 2015", 10 pgs.

* cited by examiner

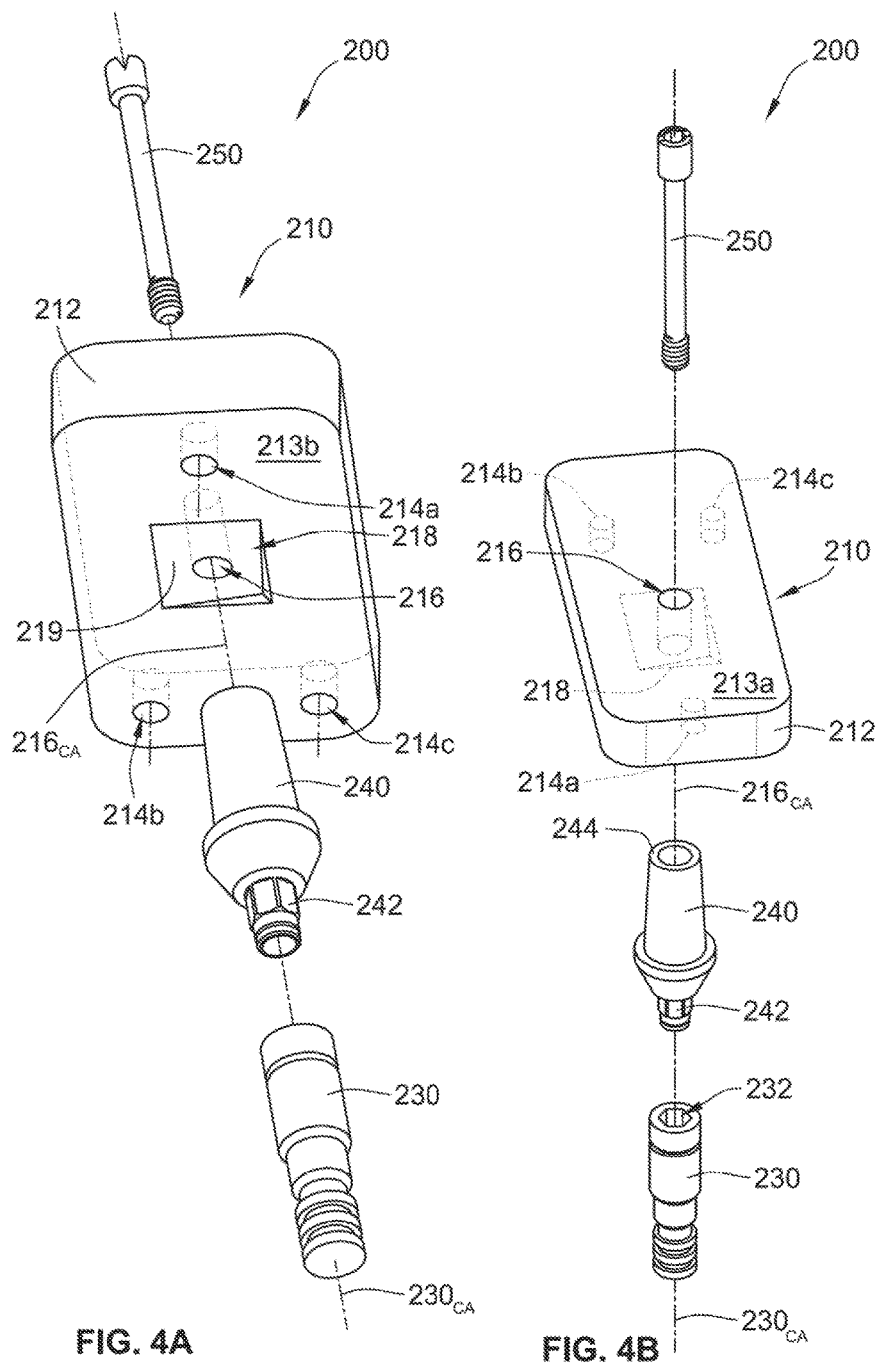

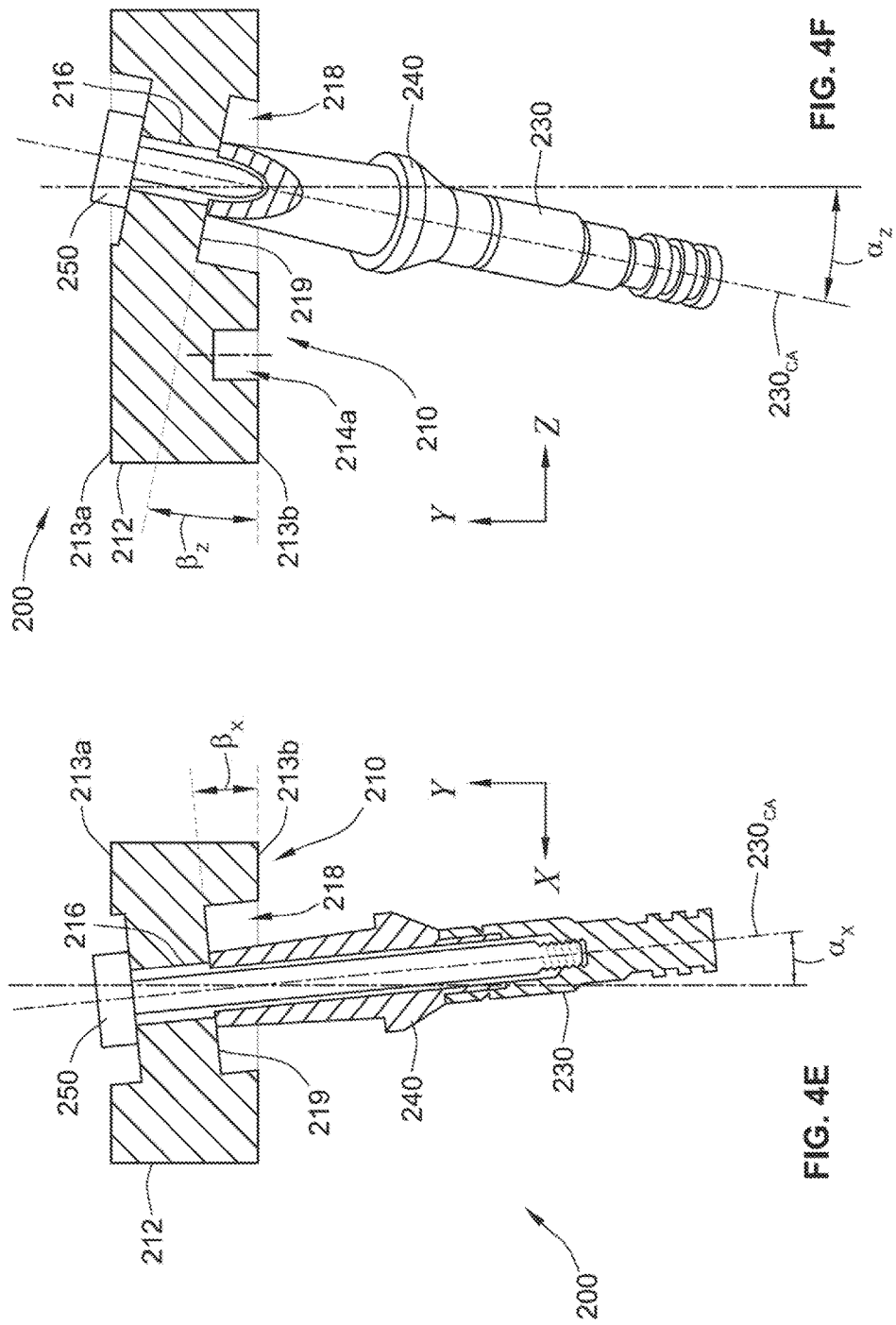

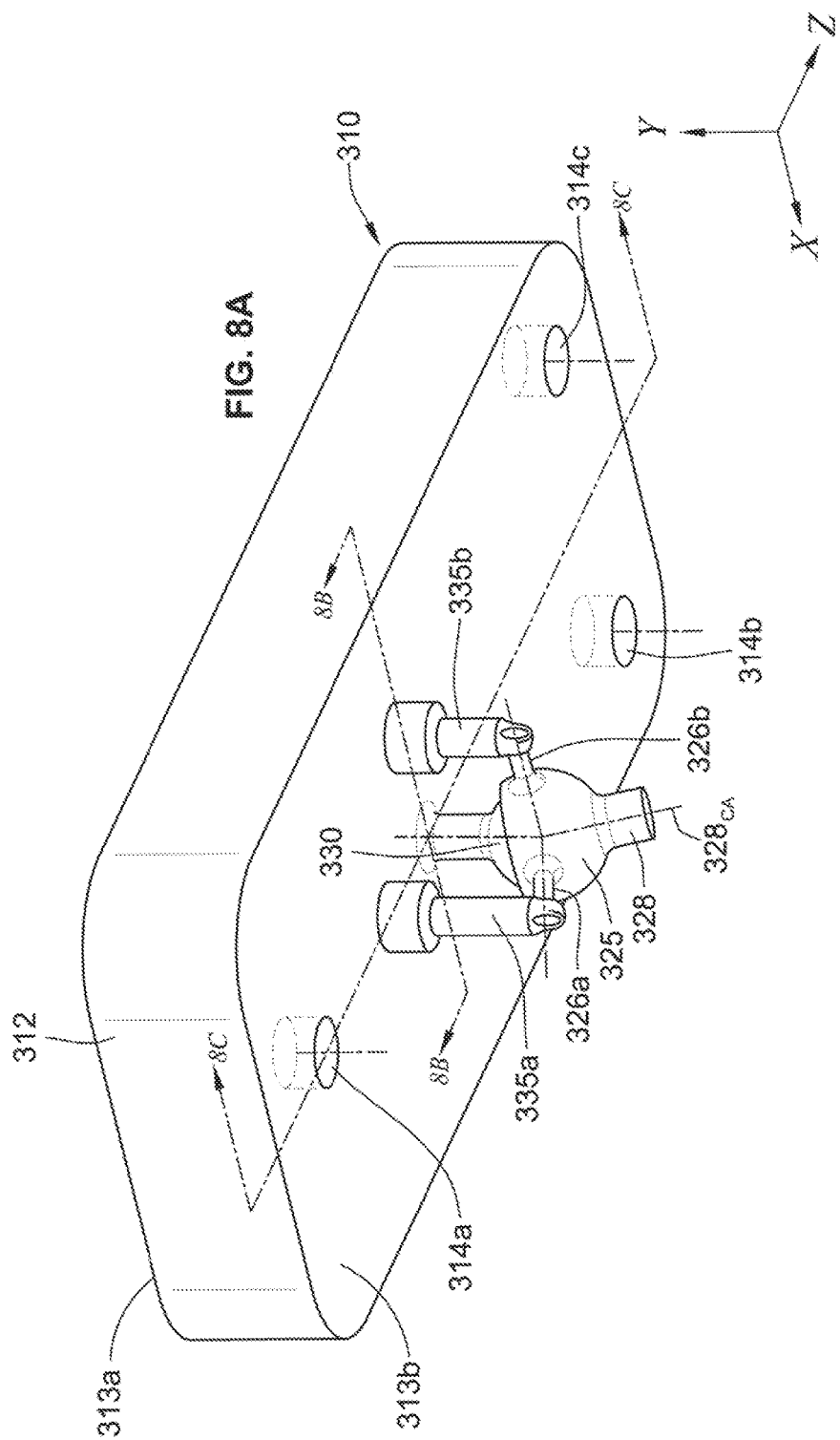

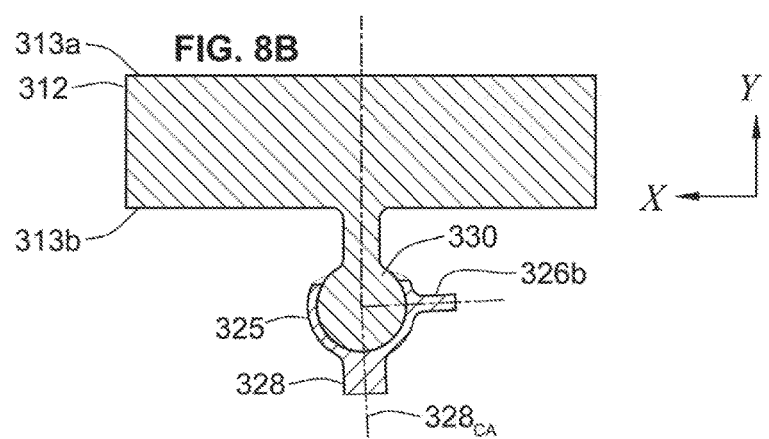
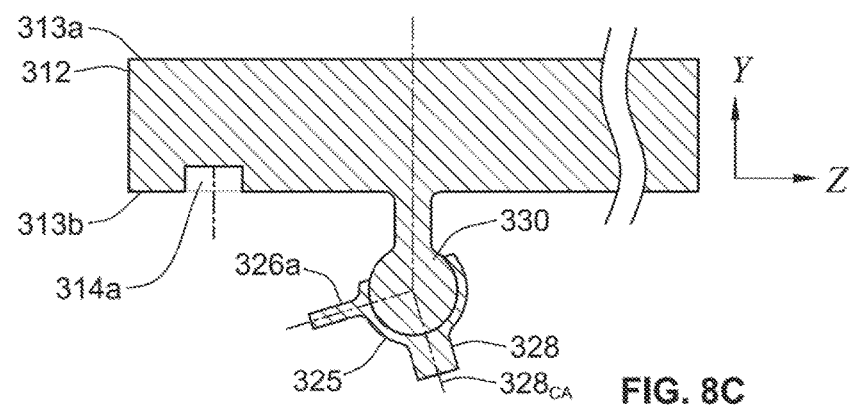

JIGS FOR PLACING DENTAL IMPLANT ANALOGS IN MODELS AND METHODS OF DOING THE SAME

This application is a divisional of prior application Ser. No. 13/727,750, filed Dec. 27, 2012, now allowed, which is hereby incorporated by reference herein in its entirety.

FIELD OF THE INVENTION

The present disclosure relates generally to developing a tooth prosthesis. More particularly, the present disclosure relates to using a placement jig to place a dental implant analog in a model of a patient's mouth for use in creating a tooth prosthesis.

BACKGROUND OF THE INVENTION

The dental restoration of a partially or wholly edentulous patient with artificial dentition is typically done in two stages. In the first stage, an incision is made through the gingiva to expose the underlying bone. An artificial tooth root, in the form of a dental implant, is placed in the jawbone for osseointegration. The dental implant generally includes a threaded bore to receive a retaining screw for holding mating components thereon. During the first stage, the gum tissue overlying the implant is sutured and heals as the osseointegration process continues.

Once the osseointegration process is complete, the second stage is initiated. Here, the gingival tissue is re-opened to expose an find of the dental implant. A healing component or healing abutment is fastened to the exposed end of the dental implant to allow the gingival tissue to heal therearound. It should be noted that the healing abutment can be placed on the dental implant immediately after the implant has been installed and before osseointegration, thereby, for some situations, combining the osseointegration step and gingival healing step into a one-step process.

Implant dentistry restorative methods have advanced beyond requiring a level (e.g., (e.g., dental implant level) impression as the starting point for developing a final dental prosthesis. In some such cases pre-defined scan bodies (e.g., Encode Healing Abutments available from Biomet 3i, LLC) are assembled to the dental implants prior to and/or during the gingival healing stage. The pre-defined can bodies include scannable features (e.g., markers) that, when scanned and interpreted, provide information about the location and orientation of the underlying dental implant that is used in developing the final dental prosthesis.

A model of the patient's mouth is typically created for use in developing the final dental prosthesis. The model of the patient's mouth is modified to include a dental implant analog that is placed/installed in the model at a position corresponding to the position of the actual underlying dental implant in the patient's mouth. Some prior methods of placing the dental implant analog in the model of the patient's mouth required the use of a robot. Although such methods using robotic placement provide benefits (e.g., accurate placement of the dental implant analog), such methods are reliant on having robotic equipment and accompanying software. Thus, a need exists for other alternative methods for placing dental implant analogs in a model of a patient's mouth for use in developing a final dental prosthesis. The present disclosure is directed to solving these and other needs.

SUMMARY OF THE INVENTION

The present disclosure provides methods for developing and fabricating permanent patient-specific prostheses without needing robotic placement equipment. In particular, the present disclosure provides methods for using, dental implant analog placement jigs for placing a dental implant analog in a modified model of a patient's mouth for use in developing a permanent patient-specific prosthesis thereon. The placement jig can be a standard jig or a custom jig. The modified model of the patient's mouth includes a bore for receiving the dental implant analog therein at a position corresponding to the position of a dental implant installed in the patient's mouth. The modified model also includes one or more guide struts protruding from a base of the model. The placement jig is registered on the model by inserting the one or more guide struts into corresponding guide-strut receiving features in the placement jig. As such, the dental implant analog coupled to the placement jig is properly located within the bore at a position and an orientation corresponding, to the location and the orientation of the dental implant installed in the patient's mouth. The dental implant analog can then be secured to the model using a securing material (e.g., glue, epoxy, acrylic, etc.). Then the placement jig is detached from the model and the permanent patient-specific prosthesis can be formed thereon.

A method of locating a dental implant analog in a model of a patient's mouth for use in creating a tooth prosthesis includes scanning at least a portion of the patient's mouth to generate scan data. The scanned portion of the patient's mouth includes teeth and an attachment member. The attachment member includes at least one informational marker indicating the location of a dental implant installed in the patient's mouth. A three-dimensional computer model of at least a portion of the patient's mouth is created using the scan data. The three-dimensional computer model includes (i) virtual teeth that correspond with the teeth in the patient's mouth, (ii) a virtual bore at a position based on the at least one informational marker and (iii) at least one virtual guide strut positioned adjacent to the virtual teeth. A physical model of the at least a portion of the patient's mouth is fabricated using a fabrication machine based on the three-dimensional computer model. The physical model includes (i) a bore corresponding to the virtual bore, and (ii) at least one guide strut corresponding, to the at least one virtual guide strut. The at least one guide strut is used in positioning the dental implant analog within the bore of the physical model at a position and an orientation corresponding to the location and the orientation of the dental implant in the patient's mouth.

A method of locating a dental implant analog, in a model of a patient's mouth for use in creating a tooth prosthesis includes creating a three-dimensional computer model of at least a portion of the patient's mouth using scan data from to scan of the patient's mouth. The three-dimensional computer model includes (i) virtual teeth that correspond with teeth in the patient's mouth and (ii) a virtual bore at a position based on at least one informational marker on an attachment member in the patient's mouth. The at least one informational marker indicates the location and the orientation of a dental implant installed in the patient's mouth. The three-dimensional computer model further includes (iii) a virtual guide strut positioned adjacent to the virtual teeth. A physical model of the at least a portion of the patient's mouth is fabricated using a fabrication machine based on the three-dimensional computer model. The physical model includes (i) a bore corresponding, to the virtual bore, and (ii) a guide strut corresponding to the virtual guide strut. The dental implant analog is coupled to a placement jig. The placement jig includes a guide-strut receiving feature to be used in conjunction with the guide strut of the physical model in positioning the dental implant analog within the bore of the physical model at a position and an orientation corresponding to the location and the orientation of the dental implant in the patient's mouth.

A method of locating a dental implant analog in a model of a patient's mouth for use in creating a tooth prosthesis includes creating a three-dimensional computer model of at least a portion of the patient's mouth using scan data from a scan of the patient's mouth. The three-dimensional computer model includes (i) virtual teeth that correspond with teeth in the patient's mouth and (ii) a virtual bore at a position based on at least one informational marker on an attachment member in the patient's mouth. The at least one informational marker indicates the location and the orientation of a dental implant installed in the patient's mouth. The three-dimensional computer model further includes (iii) a virtual guide strut positioned adjacent to the virtual teeth. The method further includes fabricating, using a fabrication machine, a physical model of the at least a portion of the patient's mouth based on the three-dimensional computer model. The physical model includes (i) a bore corresponding to the virtual bore, and (ii) a guide strut corresponding to the virtual guide strut. The dental implant analog is coupled to an adjustable arm of a placement jig. The adjustable arm has at least two degrees of rotational freedom with respect to a base of the placement jig. The base of the placement jig further includes a guide-strut receiving feature to be used in conjunction with the guide strut of the physical model in positioning the dental implant analog, within the bore of the physical model at a position and an orientation corresponding to the location and the orientation of the dental implant in the patient's mouth.

A placement jig for locating a dental implant analog in a physical model of at least a portion of a patient's mouth for use in creating a tooth prosthesis includes a base, a guide-strut receiving feature, a throughbore, and an angled receiving feature. The base has an upper surface and a lower surface. The guide-strut receiving feature is positioned within the base and is configured to receive a guide-strut of the physical model thereby positioning the lower surface of the placement jig at a desired distance from an opening of a bore in the physical model. The throughbore is for receiving a screw therethrough. The screw is configured to be coupled with the dental implant analog, such that the dental implant analog is removably coupled to the base. The throughbore has a central axis oriented at an angle relative to the lower surface of the base. The angled receiving feature is positioned about the throughbore on the lower surface of the base. The angled receiving, feature includes a mating surface that is configured to abut a custom abutment positioned between the mating surface and the dental implant analog. The central axis of the throughbore is perpendicular to the angled receiving feature.

A placement jig for locating a dental implant analog in a physical model of at least as portion of a patient's mouth for use in creating a tooth prosthesis includes a base, a guide-strut receiving feature, and an adjustable arm. The base has an upper surface spaced from a lower surface. The guide-strut receiving feature is positioned within the base and is configured to receive a guide-strut of the physical model to position the lower surface of the placement jig a desired distance from an opening of a bore in the physical model. The adjustable arm extends from the lower surface of the base and is configured to be removably coupled to the dental implant analog. The adjustable arm has at least two degrees of rotational freedom with respect to the base.

A physical model of a patient's mouth for use in creating a tooth prosthesis includes a model base, model, teeth, a bore, and a first guide strut. The model teeth protrude from the model base. The model teeth correspond with teeth in the patient's mouth. The bore is in the model base and is configured to receive a dental implant analog therein. The bore is also positioned adjacent to at least one of the model teeth. The first guide strut protrudes from the model base and is configured to mate with a positioning jig to position the dental implant analog within the bore at a position and an orientation corresponding to the location and the orientation of a dental implant in the patient's mouth.

Additional aspects and implementations of the present disclosure will be apparent to those of ordinary skill in the art in view of the detailed description of various implementations, which is made with reference to the drawings, a brief description of which is provided below.

BRIEF DESCRIPTION OF THE DRAWINGS

The foregoing and other advantages of the disclosure will become apparent upon reading the following detailed description and upon reference to the drawings.

FIGS. 4A and 4B are an exploded perspective views of a dental implant analog placement jig assembly according to some implementations of the present disclosure;

FIGS. 4E and 4F are cross-sectional views of the assembled dental implant analog placement jig assembly of FIG. 4D;

FIG. 8A is a perspective view of a dental implant analog placement jig including an adjustable arm according to some implementations of the present disclosure; and FIGS. 8B and 8C are cross-sectional views of the dental implant analog placement jig of FIG. 8A.

Figure 1:
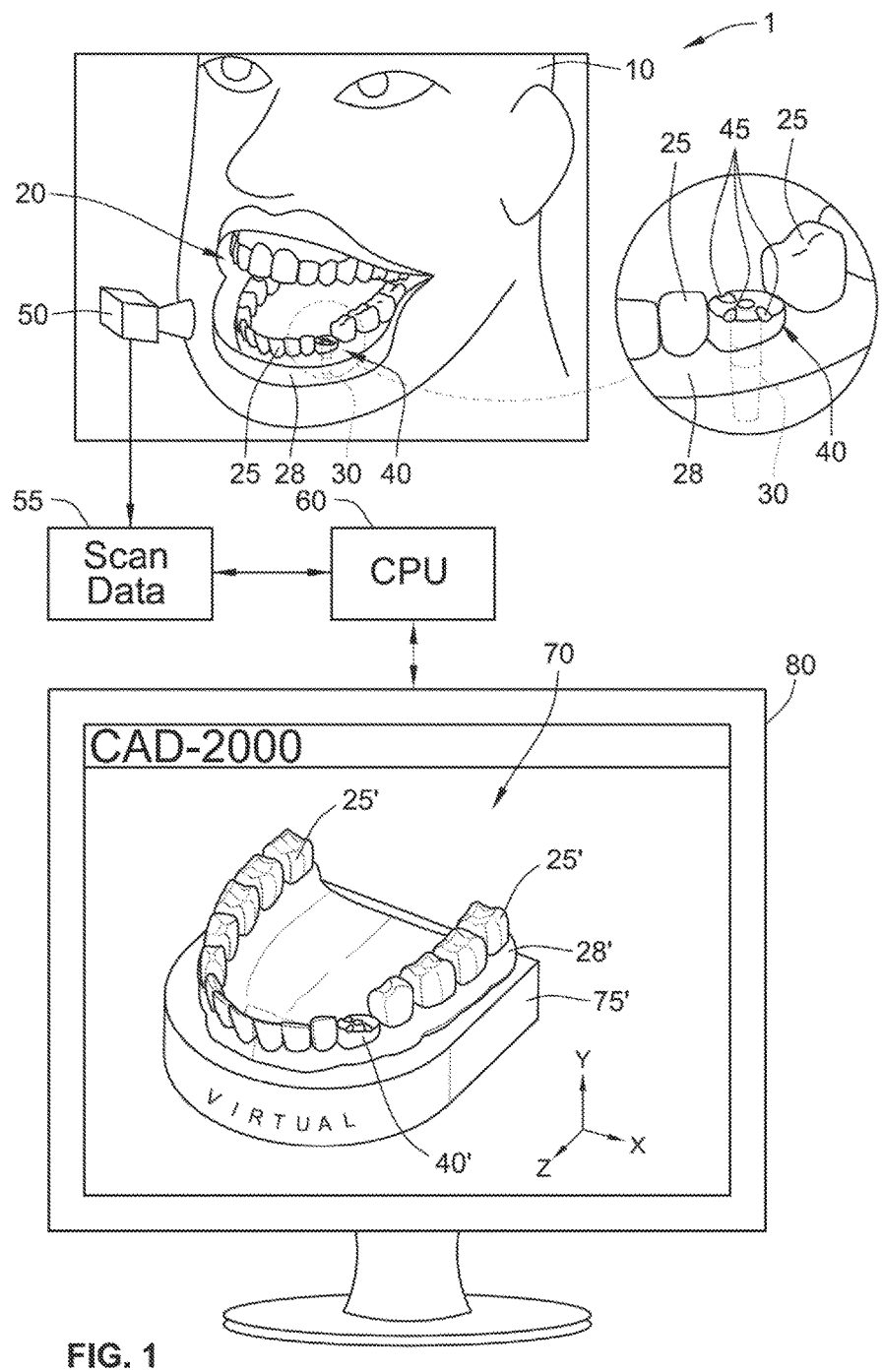
FIG. 1 is an illustrative flow diagram of a patient's mouth including an abutment installed therein being scanned and processed by a CPU to create an unmodified three-dimensional computer model of the patient's mouth according to some implementations of the present disclosure.

While the present disclosure is susceptible to various modifications and alternative forms, specific embodiments have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DESCRIPTION OF ILLUSTRATIVE EMBODIMENTS

When developing as permanent patient-specific prosthesis, the process typically begins with the installation of a dental implant in as patient's mouth. An attachment member, such as, for example, a healing abutment or an abutment, is typically attached to the dental implant and the mouth is allowed to heal therearound (e.g., osseointegration of the dental implant occurs). At some point thereafter, the patient returns to the dentist or clinician such that a model of the patient's mouth can be created for use in designing/developing and/or fabricating the permanent patient-specific prosthesis. The following disclosure includes description of a method(s) of creating such a model that can be used for designing/developing and/or fabricating the permanent patient-specific prosthesis thereon, where the model includes a dental implant analog.

The term "dental implant analog" as used herein has the meaning ascribed to it by persons of ordinary skill in the field of dental implants, dental implant systems, and related dental systems. Generally, the term "dental implant analog" refers to a component used in a model of as mouth of a patient that is used to represent the underlying dental implant installed in the patient's mouth. The dental implant analog, can be an actual dental implant that is just attached to the model of the patient's mouth instead of being installed in a real mouth of a patient. In most instances, the dental implant analog is a modified version of a dental implant installed in a patient's mouth. For example, the subgingival portion of a dental implant analog is generally different (e.g., no external threads) than the subgingival portion of a dental implant (e.g., external threads) installed in a patient's mouth.

Referring to FIG. 1, an illustrative flow diagram 1 of a mouth 20 of a patient 10 being scanned by an intraoral scanner 50 to create an unmodified virtual three-dimensional computer model 70 of the patient's mouth 20 is shown. The patient's mouth 20 includes teeth 25, gingival tissue 28, a dental implant 30 installed therein, and an attachment member such as, for example, a scanning member and/or an abutment 40 attached to the dental implant 30. As shown in FIG. 1, the scanning member/abutment 40 is a healing abutment such as, for example, an ENCODE® Healing abutment available from Biomet 3i, LLC; although the scanning member/abutment 40 can be any type of scanning member. The abutment 40 includes one or more informational markers 45 that when scanned by the scanner 50 and interpreted by, for example, the CPU 60 provide information about the location (e.g., position of a table of the dental implant along the Y-axis) and orientation (e.g., rotational position of a non-round feature of the dental implant about the Y-axis) of the underlying dental implant 30. Additional details on abutments, informational markers, uses of the same, and interpreting the same can be found in U.S. Pat. No. 6,790,040, which is hereby incorporated by reference herein in its entirety.

The scanner 50 used to scan the mouth 20 of the patient 10 can be any type or kind of scanner, such as, for example, a 3D dental scanner (e.g., model nos. D500, D700, D710, D800, and D810) available from 3Shape A/S located in Copenhagen. Denmark or a LAVA Chairside Oral Scanner available from 3M located in Saint Paul, Minn. The scanning of the mouth 20 generates scan data 55 associated with the teeth 25, the gingival tissue 28, and the abutment 40 that can be used by, for example, the CPU 60 to create the unmodified virtual three-dimensional computer model 70 of the mouth 20 of the patient 10. Thus, the scanning of the mouth 20 captures all of the contours, sizes, and shapes of the teeth 25, gingival tissue 28, and abutment. 40 in a digital format that can be displayed as the unmodified virtual three-dimensional computer model 70 of the mouth 20 of the patient 10 on a display device 80 (e.g., computer monitor). Specifically, at a minimum, the area of the mouth 20 including the abutment 40 and the immediately adjacent teeth 25 and gingival tissue 28 is scanned such that the unmodified virtual three-dimensional computer model 70 is a complete virtual replica of the scanned area of the mouth 20.

The unmodified virtual three-dimensional computer model 70 of the patient's mouth 20 includes virtual teeth 25', virtual gingival tissue 28', and a virtual abutment 40'. Each of the virtual teeth 25', virtual gingival tissue 28', and virtual abutment 30 is coupled to a virtual base 75' for supporting the same thereon. The virtual teeth 25' correspond to the teeth 25 in the mouth 20 of the patient 10. Similarly, the virtual gingival tissue 28' and the virtual abutment 40' correspond to the gingival tissue 28 and the abutment 40, respectively. Notably, the unmodified virtual three-dimensional computer model 70 does not include a virtual dental implant that corresponds with the dental implant 30 as the dental implant 30 is not viewable and/or scannable by the scanner 50 (e.g., the dental implant 30 is obscured by the gingival tissue 28 and/or the abutment 40).

Figure 2:
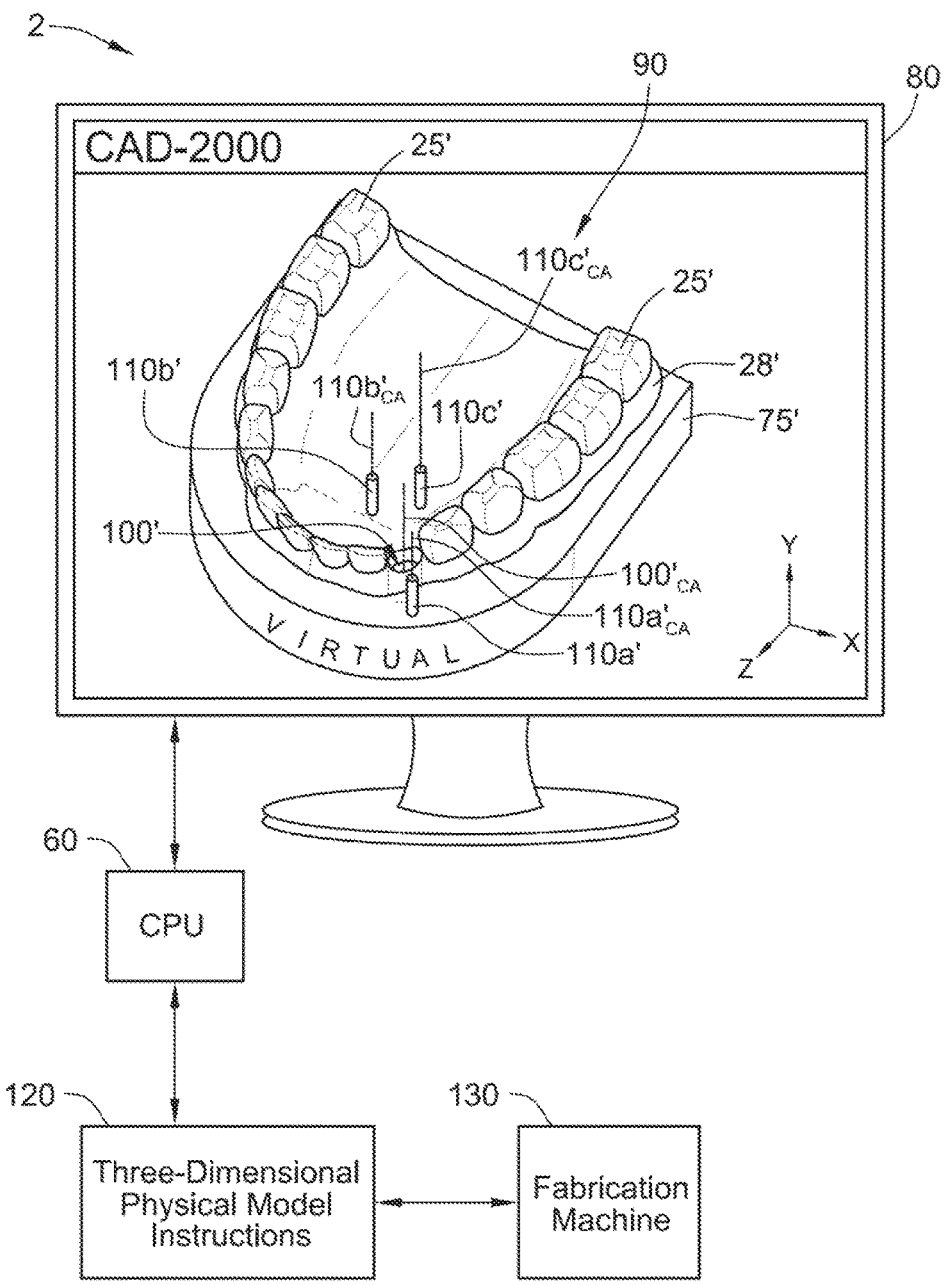
FIG. 2 is an illustrative flow diagram of a modified version of the three dimensional computer model of the patient's mouth of FIG. 1 being processed by a CPU and sent to a fabrication machine.

The unmodified virtual three-dimensional computer model 70 is modified into a modified virtual three-dimensional computer model 90, shown in the illustrative flow diagram 2 of FIG. 2. Specifically, the unmodified virtual three-dimensional computer model 70 is virtually modified into the modified virtual three-dimensional computer model 90 by virtually removing the virtual abutment 40' (e.g., the modified virtual three-dimensional computer model 90 lacks the virtual abutment 40'). Additionally, the unmodified virtual three-dimensional computer model 70 is virtually modified into the modified virtual three-dimensional computer model 90 by virtually creating a virtual bore 100' and by virtually creating one or more virtual guide struts 110a-c' adjacent to the virtual bore 100', as shown in FIG. 2.

The virtual bore 100' is generally cylindrical and has a central axis $100'_{CA}$. The central axis $100'_{CA}$ of the virtual bore 100' is substantially vertical (e.g., parallel with vertical or the Y-axis). Each of the virtual guide struts 110a-c' has as generally cylindrical rod-like shape with respective central axes $110a\text{-}c'_{CA}$. The central axes $110a\text{-}c'_{CA}$ of the virtual guide struts 110a-c' are also substantially vertical (e.g., parallel with vertical or the Y-axis).

In some alternative implementations, the central axis $100'_{CA}$ of the virtual bore 100' and/or the central axes $110a\text{-}c'_{CA}$ of the virtual guide struts 110a-c' can be at an angle with respect to vertical (e.g., the Y-axis), which is not shown in the FIGS. In some such alternative implementations, the central axis $100'_{CA}$ of the virtual bore 100' is parallel with the central axes $110a\text{-}c'_{CA}$ of the virtual guide struts 110a-c'. In other such alternative implementations, the central axis $100'_{CA}$ of the virtual bore 100' is not parallel with the central axes $110a\text{-}c'_{CA}$ of the virtual guide struts 110a-c'.

In order to determine the location (e.g., X-Z plane position) and orientation (e.g., angle of the central axis with respect to the Y-axis) for the virtual bore 100' and/or the virtual guide struts 110a-c' in the modified virtual three-dimensional computer model 90, the CPU 60 analyzes the scan data 55 using, for example, one or more software programs. In particular, the one or more software programs analyze and/or determine information associated with the informational markers 45 on the abutment 40, which provides information about the location and orientation of the actual underlying, dental implant 30 in the mouth 20 of the patient 10. Based on the determined location and orientation of the actual underlying dental implant 30. The one or more software programs determine appropriate locations and orientations for the virtual bore 100' and the virtual guide struts 110*a-c*' in the modified virtual three-dimensional computer model 90.

Examples of the one or more software programs used to create the unmodified virtual three-dimensional computer model 70 and the modified virtual three-dimensional computer model 90 include CAD Design Software available from 3Shape A/S located in Copenhagen, Denmark; DentalCAD available from exocad GmbH in Darmstadt, Germany; and DentCAD available from Delcam plc in Birmingham, United Kingdom.

Figure 3:
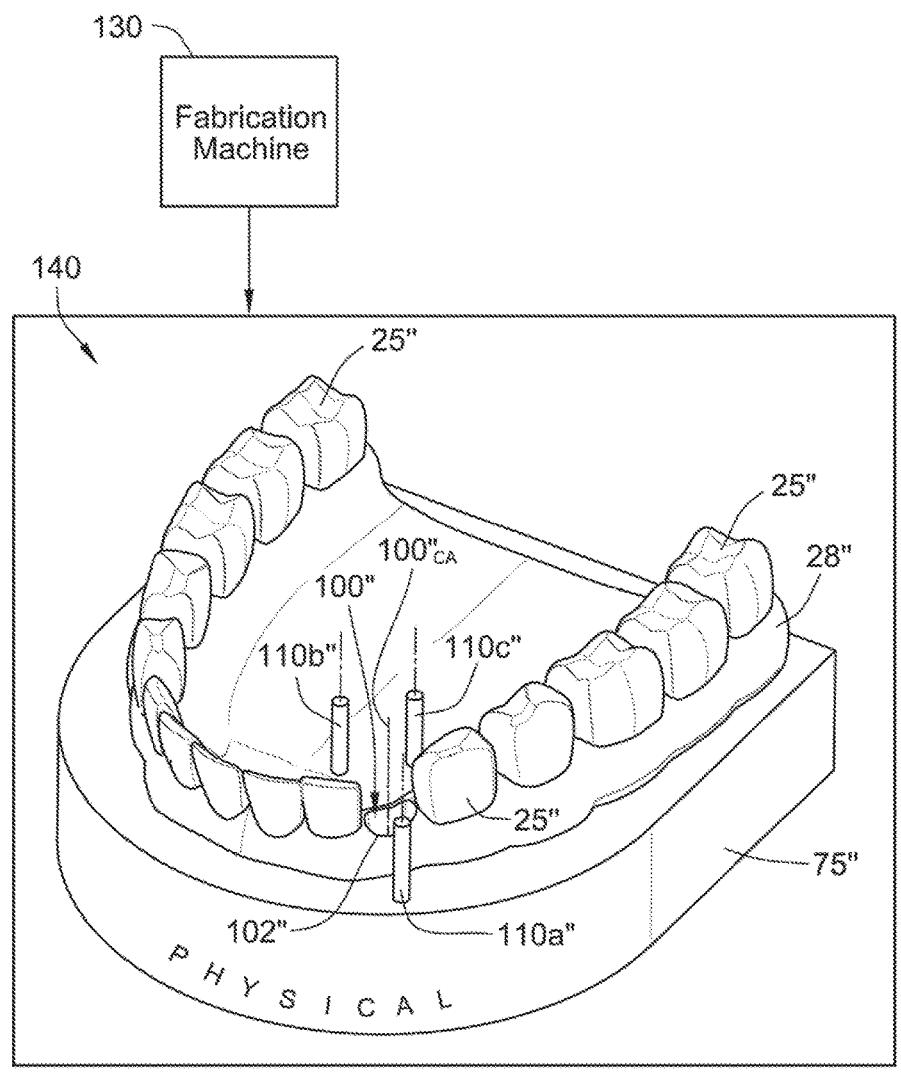
FIG. 3 is an illustrative flow diagram of the fabrication machine of FIG. 2 creating a physical model of the patient's mouth including a bore and a guide struts according to some implementations of the present disclosure.

After creating the modified virtual three-dimensional computer model 90, three-dimensional physical model instructions 120 (FIG. 2) are generated by, for example, the CPU 60. The three-dimensional physical model instructions 120 are sent to and/or transferred from the CPU 60 to a fabrication machine 130, such as for example, a rapid-prototyping machine and/or a milling machine, for creating a modified physical model 140 (FIG. 3) of the mouth 20 of the patient 10. As shown in FIG. 3, the modified physical model 140 is substantially an exact replica of the modified virtual three-dimensional computer model 90.

Specifically, the modified physical model 130 includes model teeth 25", model gingival tissue 28", a model bore 100", and model guide struts 110*a-c*". Each of the model teeth 25", model gingival tissue 28", and model guide struts 110*a-c*" is coupled to a model base 75" for supporting the same thereon. Additionally, the model bore 100" is formed within the model base 75". The model teeth 25" correspond to the virtual teeth 25' in the modified three-dimensional computer model 90 of the mouth 20 of the patient 10. Similarly, the model gingival tissue 28" corresponds to the virtual gingival tissue 28'; the model bore 100" corresponds to the virtual bore 100'; and the model guide struts 110*a-c*" correspond to the virtual guide struts 110*a-c*'. Additionally, the model base 75", the model teeth 25", the model gingival tissue 28", and the model guide struts 110*a-c*" are all made of the same material. For example, if a rapid prototype machine is used to fabricate the modified physical model 140, the model base 75", the model teeth 25", the model gingival tissue 28", and the model guide struts 110*a-c*" are all made of the same rapid prototype material. For another example, if a milling machine (e.g., a computer numerical controlled (CNC) milling machine) is used to fabricate the modified physical model 140, the model base 75", the model teeth 25", the model gingival tissue 28", and the model guide struts 110*a-c*" are all milled from a block of material (e.g., plastic, wax, metal, etc.).

With the modified physical model 140 created (FIG. 3), a dental implant analog is ready to be placed and secured thereto for use in developing a final dental prosthesis on the modified physical model 140. By the term "modified physical model" it is meant that the modified physical model 140 is a modified version of a model of the mouth 20 of the patient 10. Specifically, the modified physical model 140 is modified as compared to an unmodified physical model (not shown) of the mouth 20 of the patient 10 in that the modified physical model 140 includes the model, bore 100" and the model guide struts 110*a-c*", which are not natural elements of the mouth 20 of the patient 10.

A dental implant analog can be placed and secured to the modified physical model 140 using a placement jig according to several aspects of the present disclosure. For example, as shown in FIGS. 4A-4F, a placement jig assembly 200 includes a placement jig 210, a dental implant analog 230, a spacer and/or custom abutment 240, and a fastener 250 (e.g., a screw). The placement jig assembly 200 has an unassembled configuration (FIGS. 4A and 4B) and an assembled configuration (FIGS. 4C-4F).

Figure 4C:
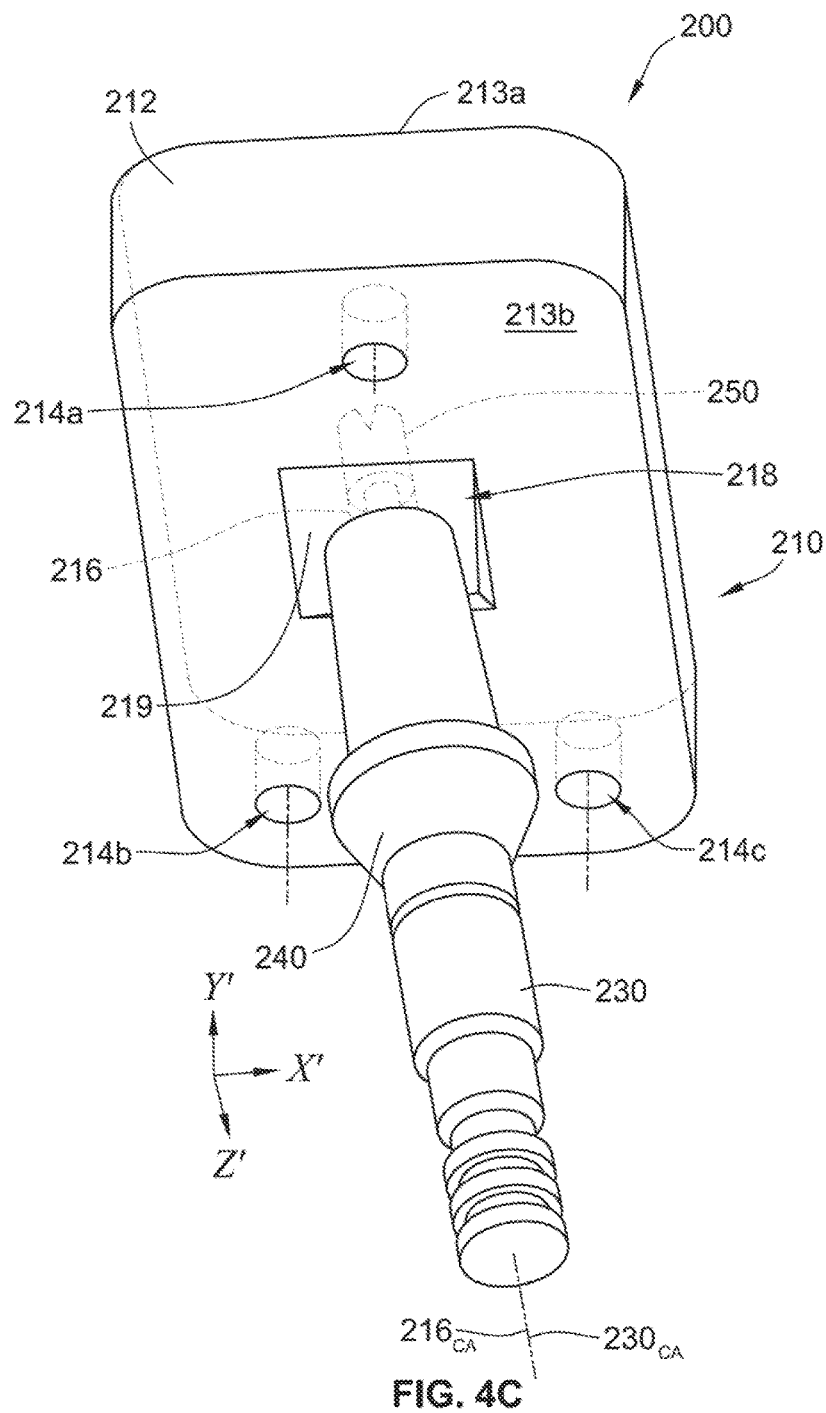
FIGS. 4C and 4D are assembled perspective views of the dental implant analog placement jig assembly of FIGS. 4A and 4B.
Figure 4D:
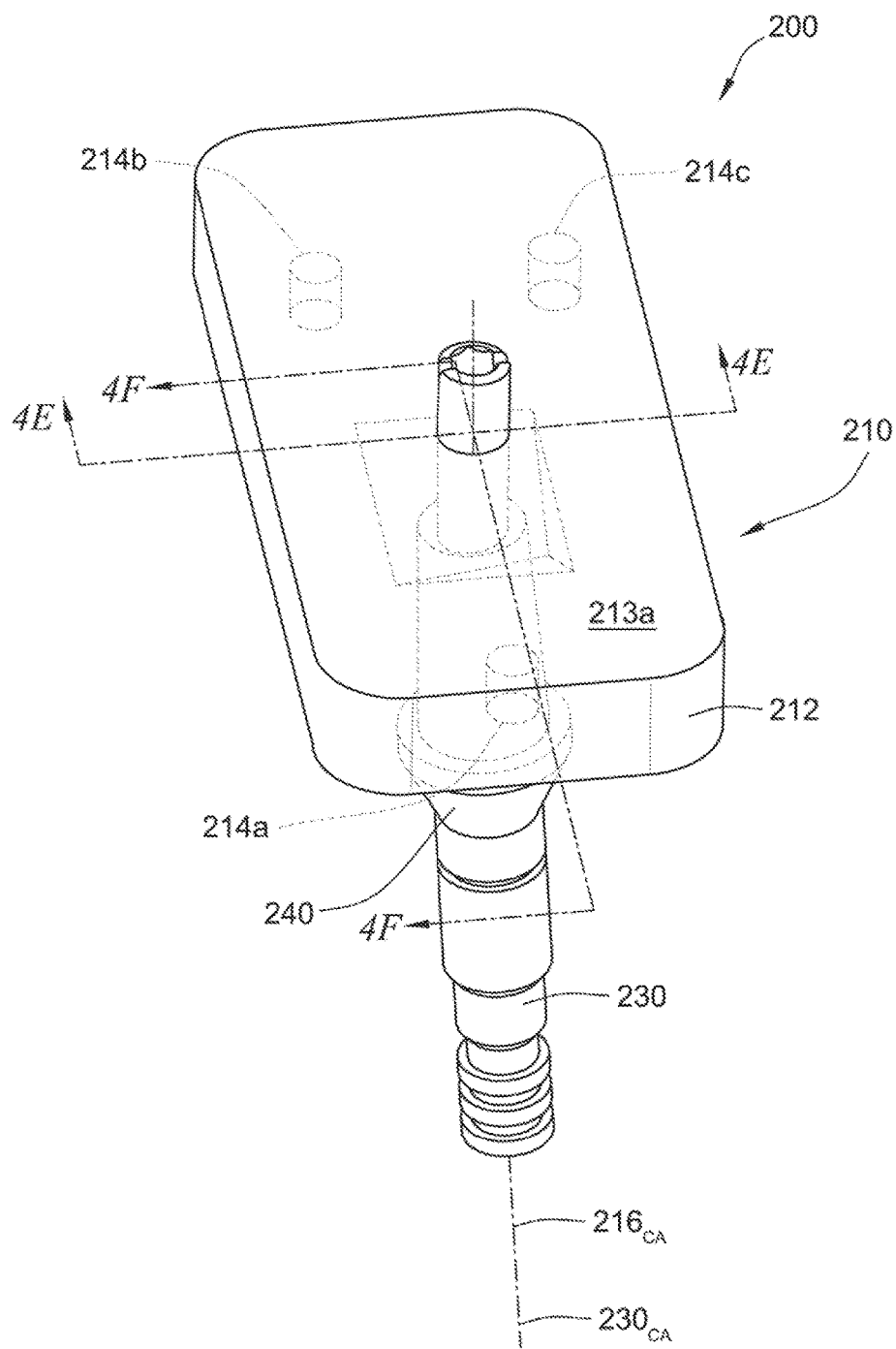

To assemble the placement jig assembly 200, the components of the placement jig, assembly 200 are initially arranged as shown in FIGS. 4A and 4B. The custom abutment 240 is non-rotationally coupled to the dental implant analog 230 via, for example, complementary non-round features of the dental implant analog (e.g., a polygonal socket 232 shown in FIG. 4B) and the custom abutment 240 (e.g., a polygonal boss 242 shown in FIGS. 4A and 4B). The custom abutment 240 is then engaged (e.g., non-rotationally engaged) with the placement jig 210 as shown in FIGS. 4C and 4D and the fastener 250 is partially positioned through a throughbore 216 of the placement jig 210 and removably coupled to an internal-partially threaded bore (shown in FIG. 4E) of the dental implant analog 230. When the placement jig assembly 200 is so assembled (FIGS. 4C-4F), the placement jig assembly 200 can be used to place the dental implant analog 230 in the modified physical model 140 (FIG. 3) at a position and an orientation corresponding to the position and orientation of the actual underlying dental implant 30 in the mouth 20 of the patient 10 (FIG. 1).

Figure 5:
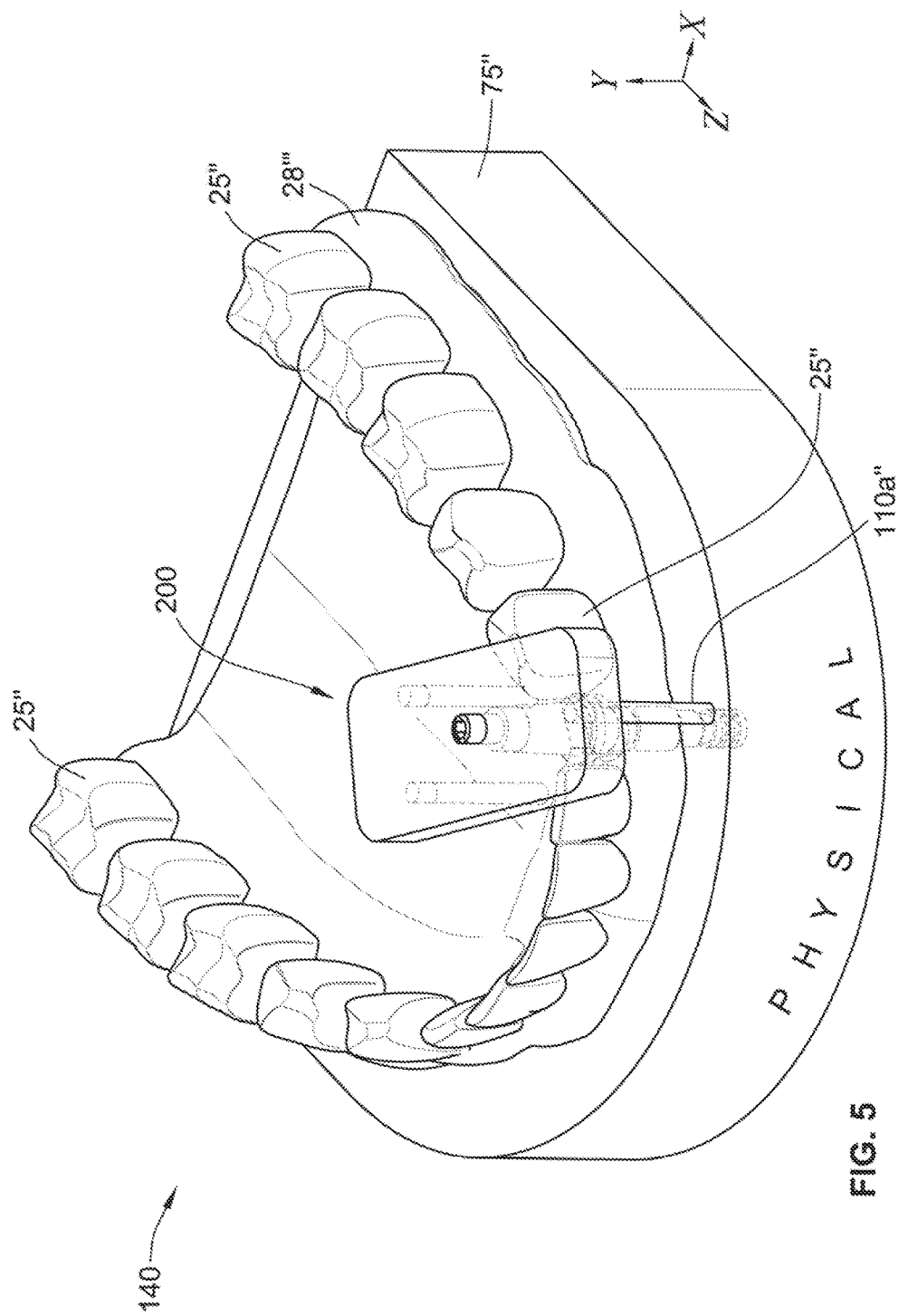
FIG. 5 is a perspective view of the assembled dental implant analog placement jig assembly of FIGS. 4C-4F registered on the physical model of the patient's mouth of FIG. 3.

Referring generally to FIGS. 4A-4F, the placement jig 210 includes a base 212 including an upper surface 213*a* (best shown in FIGS. 4A and 4D) and a lower surface 213*b* (best shown in FIGS. 4A and 4C). The upper and lower surfaces 213*a,b* are generally planar, but can have other non-planar and/or partially non-planar shapes. The placement jig 210 also includes guide-strut receiving features 214*a-c*, the throughbore 216, and an angled receiving feature 218. Each of the guide-strut receiving features 214*a-c* is sized and positioned within the base 212 to receive a corresponding one of the model guide struts 110*a-c*" (FIG. 3) of the modified physical model 140 to register the placement jig assembly 200 (FIGS. 4B-4E) on the modified physical model 140 (FIG. 3) as shown in FIG. 5.

Once registered, the lower surface 213*b* (FIGS. 4A and 4C) of the base 212 of the placement jig 210 is positioned at a selected and/or desired distance from a model opening 102" (FIG. 3) of the model bore 100". In particular, the model guide struts 110*a-c*" each has a selected and/or determined length such that registration of the placement jig 210 with the modified physical model 141) causes the lower surface 213*b* of the base 212 to be positioned at the selected and/or desired distance from the model opening 102". As such, the dental implant analog 230 coupled to the placement jig 210 can be automatically positioned at a position (e.g. a height along the Y-axis) within the model bore 100" corresponding to a position of the actual underlying dental implant 30 (FIG. 1) in the mouth 20 of the patient 10.

The throughbore 216 of the placement jig 210 passes from the upper surface 213*a* of the base 212 to the angled receiving feature 218. The throughbore 216 provides access for the fastener 250 to be received through the placement jig 210 and to be coupled to the dental implant analog 230 as best shown in FIG. 4E.

The angled receiving feature 218 of the placement jig 210 is positioned about the throughbore 216 on the lower surface 213b of the base 212 as best shown in FIG. 4A. The angled receiving feature 218 includes a mating surface 219 for engaging (e.g., abutting and/or touching) a top edge 244 (FIG. 4B) of the custom abutment 241) when the placement jig assembly 200 is assembled (e.g., FIGS. 4C-4F). The mating surface 219 is generally planar and is at an angle with respect to the lower surface 213b of the base 212, which is best shown in FIGS. 4E and 4F. In addition to, or in lieu of, the angled receiving feature 218 including the mating surface 219, the angled receiving feature 218 can include a non-round bore-type portion for receiving at least a portion of the custom abutment 240 therein in a non-rotational fashion (not shown).

As shown in FIGS. 4E and 4F, the mating surface 219 is at an angle with respect to the horizontal plane (e.g., the X-Z plane). Additionally, the angle of the mating surface can have X and Z components (e.g., a compound angle), such as the exemplary mating surface 219 of the present disclosure, which has an X-component as illustrated by angle $\beta_x$ (FIG. 4E), and a Z-component as illustrated by angle $\beta_z$ (FIG. 4F). As such, when the dental implant analog 230 is coupled to the placement jig 210 via, the fastener 250—with the custom abutment 240 between the dental implant analog 230 and the mating surface 219—a central axis $230_{CA}$ of the dental implant analog 230 is at an angle with respect to vertical (e.g., the Y-axis). Additionally, the angle of the central axis $230_{CA}$ has X and Z components, such as the exemplary central axis $230_{CA}$ of the dental implant analog 230 of the present disclosure, which has an X-component as illustrated by angle $\alpha_x$ (FIG. 4E), and a Z-component as illustrated by angle $\alpha_z$ (FIG. 4F).

The angle of the central axis $230_{CA}$ of the dental implant analog 230 with respect to vertical (e.g., the Y-axis) corresponds to (e.g., is substantially the same as) an angle of a central axis (not shown) of the underlying dental implant 30 installed in the mouth 20 of the patient 10. In order for the angle of the central axis $230_{CA}$ of the dental implant analog 230 to correspond to the central axis (not shown) of the underlying dental implant 30 (FIG. 1), the angled receiving feature 218 is selected and/or designed with the mating surface 219 having the angle with respect to the horizontal plane as described herein and as shown in FIGS. 4E and 4F. Thus, it should be understood that for substantially all modified physical models of patients' mouths (e.g., the modified physical model 140) made in accordance with the disclosed aspects herein, the angled receiving feature 218 will likely include a mating surface at a different angle with respect to horizontal as it is unlikely that two dental implants will be installed in a patient's mouth at the same angle. Methods for designing and/or fabricating such angled receiving features are disclosed below.

Further, in addition to the central axis $230_{CA}$ of the dental implant analog 230 being at an angle with respect to vertical, a central axis $216_{CA}$ (FIG. 4A) of the through bore 216 is oriented at the same angle relative to the lower surface 213b of the base 212, which aids in the attachment of the dental implant analog 230 and the custom abutment 240 to the placement jig 210 as shown in FIGS. 4C-4F. Further the central axis $216_{CA}$ (FIG. 4A) of the through bore 216 is perpendicular to the mating surface 219 of the angled receiving feature 218.

Referring to FIG. 5, the placement jig assembly 200 is registered with the modified physical model 140. Specifically, the placement jig assembly 200 is registered by inserting the dental implant analog 230 (FIG. 4B) into the model bore 100" (FIG. 3) and by aligning and inserting the model guide struts 110a-c" into the guide-strut receiving features 214a-c (FIGS. 4A and 4C) of the placement jig 210. To accommodate for the angle $\alpha_{x,z}$ of the dental implant analog 230 when the model guide struts 110a-c" align with the guide-strut receiving features 214a-c, the model bore 100" has a diameter that is larger than a maximum diameter of the dental implant analog 230. The diameter of the model bore 100" is increased as a function of the angle $\alpha_{x,z}$ of the dental implant analog 230. For example, the diameter of the model bore 100" is increased as the angle $\alpha_{x,z}$ of the dental implant analog 230 increases. As such, the diameter of the model bore 100" includes a sufficient clearance for the dental implant analog 230 to be inserted at the angle $\alpha_{x,z}$ while allowing the model guide struts 110a-c" to align with and engage the guide strut receiving features 214a-c, thereby registering the placement jig assembly 200 on the modified physical model 140 as shown in FIG. 5.

Once the placement jig assembly 201) is registered on the modified physical model 140 (FIG. 5), the dental implant analog 230 can be secured to the model base 75". Securing material, such as, for example, glue, epoxy, acrylic, plaster, cement, etc., can be used to attach the dental implant analog 230 to the model base 75". The clearance around and/or below the dental implant analog 230 in the model bore 100" is filled with the securing material and allowed to harden, thereby securely attaching the dental implant analog 230 to the modified physical model 140 in a location and orientation corresponding to the position and orientation of the actual underlying dental implant 30 in the mouth 20 of the patient 10.

Figure 6:
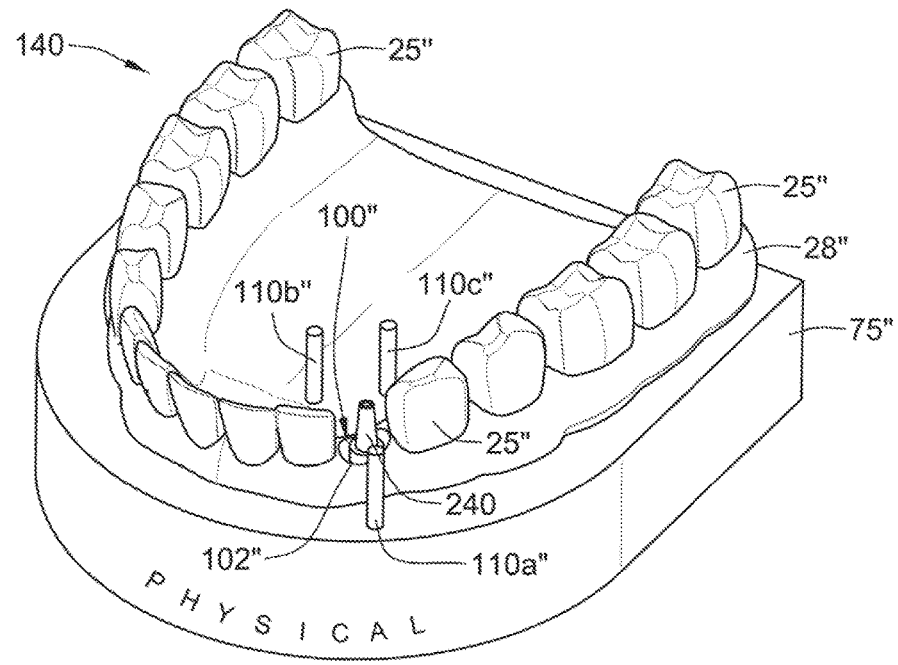
FIG. 6 is a perspective view of FIG. 5 with the dental implant analog placement jig removed from the dental implant analog placement jig assembly.

After the securing material hardens, the placement jig 210 can be removed by removing the fastener 250 as shown in FIG. 6. Removal of the placement jig 210 exposes the custom abutment 240 attached to the dental implant analog 230. The custom abutment 240 can be removably coupled to the dental implant analog 230 via second fastener (not shown) that is similar to the fastener 250, but is shorter in length. The second fastener (not shown) aids in keeping the custom abutment 240 attached to the dental implant analog 230 during fabrication of a final dental prosthesis on the modified physical model 140. A clinician and/or dentist can then fabricate a final dental prosthesis using the custom abutment 240 attached to the dental implant analog 230 on the modified physical model 140 shown in FIG. 6.

Figure 7:
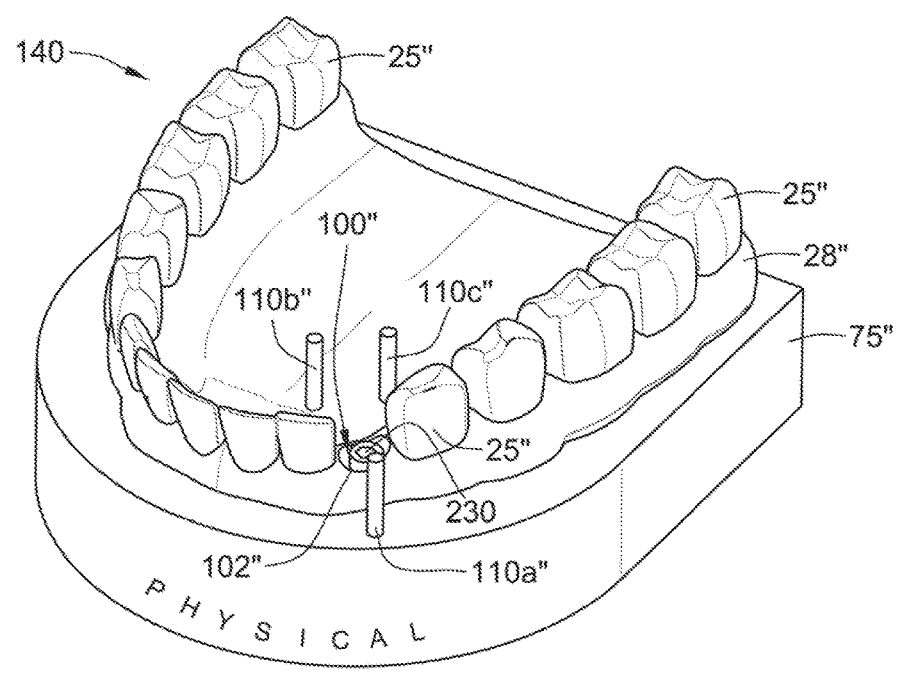
FIG. 7 is a perspective view of FIG. 6 with the abutment removed from the dental implant analog placement jig assembly revealing the installed dental implant analog.

In some alternative implementations, the custom abutment 240 is a spacer (e.g., a dummy and/or temporary abutment) and not a custom abutment designed specifically for use in the final dental prosthesis for the patient 10 (e.g., not customized for the patient 10). In such an alternative implementation, after removing the placement jig 210, the spacer/custom abutment 240 is also removed to expose the attached dental implant analog 230 as shown in FIG. 7. From there, a final dental prosthesis can be fabricated directly on the dental implant analog 230 secured to the modified physical model 140.

The custom abutment 240 is included in the placement jig assembly 200 (FIGS. 4A-4E) in part to aid in the proper vertical placement of the dental implant analog 230. Without the custom abutment 240, when a clinician attempts to register the guide strut receiving features 214a-c of the placement jig 210 with the model guide struts 110a-c", the adjacent model teeth 25" would likely obstruct and/or interfere with the proper placement of the dental implant analog 230. By including the custom abutment 240 in the placement jig assembly 200, the custom abutment 240 provides additional vertical clearance for the dental implant analog 230 to be positioned within the model bore 100" at a height along the Y-axis that corresponds to the height of the actual underlying dental implant 30 (FIG. 1) installed in the mouth 20 of the patient 10.

Alternatively, in lieu of the custom abutment 240 being, included in the placement jig assembly 200, the placement jig 210 can include a protrusion (not shown), such as for example, a rod, a column, a shaft, etc, that extends from the lower surface 213b of the base 212 to which the dental implant analog 230 is coupled. In some such alternative implementations, the protrusion (not shown) includes a non-round tip (e.g., a polygonal boss) that can non-rotationally engage a corresponding non-round feature (e.g., the polygonal socket 232) of the dental implant analog 230.

As described herein, the placement jig 210 aids in placing the dental implant analog 230 into the model bore 100" having an orientation (e.g., rotational position) that corresponds to the orientation of the underlying dental implant 30 in the mouth 21) of the patient 10. In some implementations of the present disclosure, to aid in such placement, the custom abutment 240 can include a marking (e.g., a line, an arrow, a dot, a notch, a groove, a divot, a raised pimple, etc.) on an outer surface thereof that is adjacent to the top edge 244 (FIG. 4B) of the custom abutment 240. The marking on the custom abutment 240 is aligned by, for example, as clinician or dentist, with a corresponding marking on the placement jig (e.g., on the mating surface 219, on the angled receiving feature 218, on the lower surface 213b of the base 212, etc.) to set the orientation of the dental implant analog 231) to correspond with the orientation of the underlying dental implant 30 in the mouth 20 of the patient 10. The corresponding marking, on the placement jig 210 is positioned on the placement jig 211) based on the information determined from the scanning and/or processing of the scan data 55 (FIG. 1) associated with the informational markers 45 on the abutment 40 attached to the dental implant 30 installed in the mouth 20 of the patient 10 (FIG. 1).

As shown in FIGS. 4A-4F, the placement jig 210 includes the angled receiving feature 218. In such implementations, the angled receiving feature 218 is a custom feature that is built into the placement jig 210. For example, the placement jig 210 can start out as a stock jig blank without the angled receiving feature 218 therein. The angled receiving feature 218 can be, for example, milled into the lower surface 213b of the base 212, using as milling machine (not shown), based on the modified virtual three-dimensional computer model 90 and/or the information determined from the scanning and/or processing of the scan data associated with the informational markers 45 on the abutment 40 attached to the dental implant 30 installed in the mouth 20 of the patient 10 (FIG. 1).

For another example, the placement jig 210 can be custom made by, for example, a fabrication machine (e.g., it rapid prototyping machine, a milling machine, etc.). In such implementations of the presently disclosed concepts, a virtual placement jig (not shown) is designed using, for example, the CPU 60 and one or more software programs described herein. The virtual placement jig is designed based on the modified virtual three-dimensional computer model 90. After the virtual placement jig is designed, the CPU 60 develops three-dimensional jig instructions from the designed virtual placement jig. The developed three-dimensional jig instructions are transferred and/or sent to the fabrication machine (e.g., the fabrication machine 130), which fabricates the placement jig 210 including the angled receiving feature 218 and the guide strut receiving features 214a-c.

According to some alternative implementations, the mating surface 219 of the angled receiving feature 218 is parallel and/or coplanar with the lower surface 213b of the base 212 such that the placement jig 210 essentially lacks the angled receiving feature 218. In such an alternative implementation, the central axis $216_{CA}$ of the throughbore 216 is perpendicular to (e.g., ninety degrees relative to) the lower surface 213b of the base 212 and the top edge 244 (FIG. 4B) of the custom abutment 240 directly abuts the lower surface 213b of the base 212 such that the central axis $230_{CA}$ of the dental implant analog 230 is generally perpendicular to e.g., ninety degrees relative to) the lower surface 213b. Further, in such an alternative implementation, the model guide struts 110a-c" are designed and fabricated having relatively varying heights along the Y-axis such that registering the placement jig assembly 200 on the modified physical model 140 automatically positions the dental implant analog 230 in the model bore 100" having a position and orientation corresponding, to the position and orientation of the dental implant 30 installed in the mouth 20 of the patient 10 (FIG. 1). That is, by varying the relative heights of the model guide struts 110a-c", the dental implant analog 230 can be angled relative to vertical (e.g., the Y-axis) when the placement jig assembly is registered on the modified physical model 140.

As best shown in FIGS. 4A-4D, the guide-strut receiving, features 214a-c are cylindrical bores in the base 212 of the placement jig 210. Alternatively, one or more of the guide-strut receiving features 214a-c can be a non-cylindrical or a non-round bore (e.g., a polygonal bore, etc.) having a non-round cross-section. In such alternative implementations including a guide-strut receiving feature with a non-cylindrical bore, the placement jig 210 can include only one guide-strut receiving feature and the modified physical model 140 can likewise include only one guide strut having a corresponding non-cylindrical or non-round cross-section. Such a non-round guide-strut receiving feature can be registered on such a non-round guide strut for placing the dental implant analog 230 in the model bore 100" at a position and orientation corresponding to the position and orientation of the dental implant 30 installed in the mouth 20 of the patient 10.

Now referring generally to FIGS. 8A-8C, an alternative placement jig 310 includes an adjustable arm 320 in lieu of an angled receiving feature (e.g., the angled receiving feature 218) and a throughbore (e.g., the throughbore 216). The placement jig 310 further includes a base 312 having, an upper surface 313a and a lower surface 313b, and guide-strut receiving features 314a-c that are the same as, or similar to, the base 212 having the upper surface 213a and the lower surface 213b and the guide-strut receiving features 214a-c of the placement jig 210 shown in FIGS. 4A-4F and described herein.

The adjustable arm 320 includes a pivoting member 325, a stationary member 330, and two adjusting rods 335a,b (e.g., solenoids). The pivoting member 325 moves (e.g., pivots) about the stationary member 330 that is rigidly attached to the lower surface 313b of the base 312. The adjusting rods 335a,b are also attached to the lower surface 313b of the base 312 and are able to extend in a linear fashion therefrom. The first adjusting rod 335a is coupled to a first stem 326a of the pivoting member 325 and can move the pivoting member 325 in a first degree of freedom. Similarly, the second adjusting rod 335b is coupled to a second stem 326b of the pivoting member 325 and can move the pivoting member 325 in a second degree of freedom.

Movement of the adjusting rods 335a,b relative to the lower surface 313b of the base 312 causes the pivoting member 325 to move. In particular, the adjusting rods 335a,b can be moved (e.g., extended relative to the lower surface 313b) to cause the pivoting member 325 to move (e.g., rotate and/or pivot) such that an implant analog attachment element 328 of the pivoting member 325 is oriented with its central axis $328_{CA}$ at any one of a multitude of angles with respect to vertical (e.g., Y-axis). As such, the implant analog attachment element 328 can generally be moved with two degrees of freedom with respect to the base 312 of the placement jig 310. Put another way, the angular orientation of the implant analog attachment element 328 can be adjusted by selectively extending the adjusting rods 335a,b.

The implant analog, attachment element 328 can include a non-round feature (e.g., a polygonal boss) for non-rotationally coupling with the dental implant analog 230 for placement into the modified physical model 140 in the same, or similar, manner as described above in connection with the placement jig assembly 200. In some implementations, prior to attaching the dental implant analog, or after a dental implant analog is attached to the placement jig 310, the pivoting member 325 is adjusted (e.g., moved, rotated, pivoted, etc.) such that registration of the placement jig 310 with the modified physical model 140 places the dental implant analog in the model bore 100" at a position and orientation corresponding to the position and orientation of the dental implant 30 installed in the mouth 20 of the patient 10.

The adjusting of the pivoting member 325 can be manual and/or automatic. For example, a dentist or a clinician can manually move the pivoting member 325 by directly touching and moving the pivoting member 325. In such an implementation, the placement jig 310 does not need the adjusting rods 335a,b. Further, the manual adjusting of the pivoting member 325 can be based on information associated with the modified virtual three-dimensional computer model 90.

In some other implementations, the pivoting member 325 can be moved b the model bore 100" during the registration of the placement jig 310 on the modified physical model 140 such that the central axis $230_{CA}$ of the dental implant analog 230 coupled to the placement jig 310 is substantially coaxial with the central axis $100"_{CA}$ (FIG. 3) of the model bore 100" of the modified physical model 140. In such implementations, the model bore 100" can be designed to snugly fit about the dental implant analog 230, thereby automatically positioning the dental implant analog 230.

For yet another example, the placement jig 310 can include an input device (not shown) that receives a code or similar input instruction that causes the pivoting member 325 to automatically move into a specific orientation. The code can be determined by, for example, the CPU 60 (FIG. 10 based on the information determined from the scanning and/or processing of the scan data 55 (FIG. 1) associated with the informational markers 45 on the abutment 40 attached to the dental implant 30 installed in the mouth 20 of the patient 10 (FIG. 1). In addition thereto and/or in lieu thereof, the code can be determined based on information associated with the modified virtual three-dimensional computer model 90. In such an alternative example, the input device (not shown) can be built into the base 312 and/or electronically coupled thereto (e.g., via one or more electrical wires).

The above disclosure discusses the scanning of the mouth 20 of the patient 10 (FIG. 1) including an attachment member (e.g., a scanning member/abutment 40) that includes one or more informational markers 45 that when scanned by the scanner 50 and interpreted by the CPU 60 provide information about the location (e.g., position of a table of the dental implant along the Y-axis) and orientation (e.g., rotational position of a non-round feature of the dental implant about the Y-axis) of the underlying dental implant 30. Alternatively to scanning the mouth 20 with the abutment 40 therein, the mouth 20 can lack (e.g., not include) the abutment 40 altogether during the scanning (not shown). In such alternative implementations, the upper portion of the dental implant 30 is viewable and, thus, scannable, by the scanner 50. As such, the unmodified virtual three-dimensional computer model 70 can be created by, for example, the CPU 60 using the scan data 55 to include a virtual dental implant that corresponds with the dental implant 30 installed in the mouth 20 of the patient. 10 (e.g., the dental implant 30 is no longer obscured by the abutment 40).

While the present disclosure has been described with reference to one or more particular embodiments and implementations, those skilled in the art will recognize that many changes may be made thereto without departing from the spirit and scope of the present disclosure. Each of these embodiments and implementations and obvious variations thereof is contemplated as falling within the spirit and scope of the present invention, which is set forth in the claims that follow.

What is claimed is:

1. A placement jig for locating a dental implant analog in a physical model of at least a portion of a patients mouth for use in creating a tooth prosthesis, comprising:
   a base having an upper surface and a lower surface, the upper and lower surfaces parallel to each other;
   a guide-strut receiving feature positioned within the base, the guide-strut receiving feature being configured to receive a guide-strut of the physical model thereby positioning the lower surface of the placement jig at a desired distance from an opening of a bore in the physical model;
   a throughbore positioned within the base, for receiving a screw therethrough, the screw being configured to be coupled with the dental implant analog such that the dental implant analog is removably coupled to the base, the throughbore having a central axis oriented at an angle relative to the lower surface of the base;
   a first angled receiving feature positioned about the throughbore on the lower surface of the base, the first angled receiving feature including a first mating surface that is configured to abut a custom abutment positioned between the mating surface and the dental implant analog, wherein the first mating surface is at an angle with respect to the lower surface of the base; and
   a second angled receiving feature positioned about the throughbore on the upper surface of the base, the second angled receiving feature including a second mating surface that is configured to abut the screw when the screw is coupled with the dental implant analog, wherein the second mating surface is parallel to the first mating surface,
   wherein the central axis of the throughbore being perpendicular to the first angled receiving feature and the second angled receiving feature, and wherein the guide-strut receiving feature is spaced from the angled receiving feature.

2. The placement jig of claim 1, wherein a central axis of the bore in the physical model is coaxial with the central axis of the throughbore of the placement jig in response to the guide-strut of the physical model being received within the side-strut receiving feature of the placement jig.

3. The placement jig of claim 1, wherein the guide-strut receiving feature is a cylindrical bore in the base of the placement jig.

4. The placement jig of claim 3, wherein the guide-strut receiving feature includes a non-round cross-section.

5. The placement jig of claim 1, wherein the angle of the central axis of the throughbore relative to the lower surface of the base is ninety degrees such that the first and second mating surfaces and the lower surface of the base are parallel, coplanar, or both.

6. The placement jig of claim 1, wherein the placement jig is a stock jig blank that includes the base, the guide-strut receiving feature, and the throughbore, the first and second angled receiving features are formed in the base using a milling machine that mills the first and second angled receiving features in the stock jig blank.

7. The placement jig of claim 1, wherein the placement jig is fabricated using a rapid-prototype machine.

8. A placement jig for locating a dental implant analog in a physical model of at least a portion of a patient's mouth for use in creating a tooth prosthesis, comprising;
 a base having an upper surface spaced from, a lower surface;
 a guide-strut receiving feature positioned within the base, the guide-strut receiving feature being configured to receive a guide-strut of the physical model to position the lower surface of the placement jig a desired distance from an opening of a bore in the physical model;
 an adjustable arm extending from the lower surface of the base and being configured to be removably coupled to the dental implant analog, the adjustable arm including:
  a stationary member rigidly attached to the lower surface of the base; and
  a pivoting member that is configured to move about the stationary member, the pivoting member including an implant analog attachment element configured to couple with the dental implant analog, and wherein the pivoting member has at least two degrees of rotational freedom with respect to the base,
 wherein the pivoting member includes a first adjustment element and a second adjustment element, the first and second element extending from a surface of the pivoting member, and wherein the placement jig further includes a first adjusting rod and a second adjusting rod each including a first end attached to the lower surface of the base and a second end attached to a corresponding adjustment element of the pivoting member.

9. The placement jig of claim 8, wherein the guide-strut receiving feature is a cylindrical bore in the base of the placement jig.

10. The placement jig of claim 9, wherein the guide-strut receiving feature includes a non-round cross-section.

11. The placement jig of claim 8, wherein the angular orientation of the adjustable arm is manually adjustable with respect to the base.

12. The placement jig of claim 8, wherein the angular orientation of the adjustable arm is automatically adjusted with respect to the base in response to the placement jig receiving an input.

13. A system for use in creating a tooth prosthesis, comprising:
 a physical model of a patient's mouth, including:
  a model base;
  model teeth protruding from the model base, the model teeth corresponding with teeth in the patient's mouth;
  a bore in the model base configured to receive a dental implant analog therein, the bore being positioned adjacent to at least one of the model teeth; and
  a first guide strut protruding from the model base and being configured to mate with a positioning jig to position the dental implant analog within the bore at a position and an orientation corresponding to the location and the orientation of a dental implant in the patient's mouth; and
 a placement jig for locating a dental implant analog in the physical model of the patient's mouth, the placement jig including:
  a base having an upper surface and a lower surface;
  a guide-strut receiving feature positioned within the base, the guide-strut receiving feature being configured to receive the first guide strut of the physical model thereby positioning the lower surface of the placement jig at a desired distance from an opening of the bore in the physical model; and
  an angled receiving feature positioned on the lower surface of the base, wherein the angled receiving feature includes a mating surface that is angled relative to the lower surface of the placement jig.

14. The system of claim 13, wherein the model base, the model teeth, and the first guide strut are all made of the same material.

15. The system of claim 13, wherein the first guide strut and a central axis of the bore in the model base are at an angle a with respect to vertical such that in response to the first guide strut mating with the positioning jig, the dental implant analog is positioned within the bore with its central axis at the angle a with respect to vertical.

16. The system of claim 15, wherein the angle a is based on an angle of a central axis of the dental implant in the patient's mouth with respect to vertical.

17. The system of claim 13, wherein at least a portion of the first guide strut includes a non-round cross-section.

18. The system of claim 13, further including a second guide strut, the second guide strut protruding from the model base adjacent to a first side of the bore and the first guide strut protruding front the model base adjacent to a second opposing side of the bore.

19. The system of claim 13, wherein the dental implant analog is coupled to the positioning jig with a custom abutment positioned between the placement jig and the dental implant analog.

20. The system of claim 13, wherein the first guide strut is configured to be received within a guide-strut receiving feature of the placement jig to position the denial implant analog within the bore at the position corresponding to the location of the dental implant in the patient's mouth.

* * * * *